(12) United States Patent
Fallin et al.

(10) Patent No.: US 8,388,655 B2
(45) Date of Patent: *Mar. 5, 2013

(54) COMPACT LINE LOCKS AND METHODS

(75) Inventors: T. Wade Fallin, Hyde Park, UT (US); M. Mary Sinnott, Logan, UT (US)

(73) Assignee: IMDS Corporation, Logan, UT (US)

( * ) Notice: Subject to any disclaimer, the term of this patent is extended or adjusted under 35 U.S.C. 154(b) by 339 days.

This patent is subject to a terminal disclaimer.

(21) Appl. No.: 12/754,774

(22) Filed: Apr. 6, 2010

(65) Prior Publication Data

US 2010/0191285 A1  Jul. 29, 2010

Related U.S. Application Data

(63) Continuation of application No. 11/125,885, filed on May 9, 2005, now Pat. No. 7,722,644, which is a continuation-in-part of application No. 10/459,375, filed on Jun. 11, 2003, now Pat. No. 7,150,757, and a continuation-in-part of application No. 10/936,376, (Continued)

(51) Int. Cl.
*A61B 17/04* (2006.01)
*A61B 17/82* (2006.01)
*A61B 17/58* (2006.01)
*F16G 11/00* (2006.01)

(52) U.S. Cl. ......... 606/232; 606/74; 606/103; 24/129 R

(58) Field of Classification Search ............ 606/74, 606/103, 158, 232; 24/115 R, 129 R, 130, 24/129 B, 129 W See application file for complete search history.

(56) References Cited

U.S. PATENT DOCUMENTS

| | | | |
|---|---|---|---|
| 757,820 A * | 4/1904 | Lykke | 24/130 |
| 1,452,338 A | 4/1923 | Flowers | |
| 1,782,625 A * | 11/1930 | Neuberger | 24/129 R |
| 2,441,336 A | 5/1948 | Sova | |
| 3,409,014 A | 11/1968 | Shannon | |
| 3,678,543 A | 7/1972 | Hobbs | |
| 3,715,782 A | 2/1973 | Newell | |
| 3,785,009 A | 1/1974 | Nysten | |
| 3,880,166 A * | 4/1975 | Fogarty | 606/158 |
| 3,910,281 A | 10/1975 | Kletschka et al. | |
| 3,976,079 A | 8/1976 | Samuels et al. | |
| 3,993,076 A * | 11/1976 | Fogarty | 606/158 |
| 4,034,443 A | 7/1977 | Turner | |
| 4,105,349 A | 8/1978 | Kupperman et al. | |
| 4,280,435 A | 7/1981 | Loomis | |
| 4,477,947 A | 10/1984 | Lyons | |
| 4,480,357 A | 11/1984 | Cummins | |
| 4,480,358 A | 11/1984 | Barling et al. | |

(Continued)

FOREIGN PATENT DOCUMENTS

| EP | 861050 B1 | 6/2004 |
|---|---|---|
| EP | 1430840 A2 | 6/2004 |

(Continued)

*Primary Examiner* — Julian Woo

(74) *Attorney, Agent, or Firm* — Peter K. Johnson; James Larson; James Pinkston

(57) ABSTRACT

A line lock includes a body at least partially bounding two passageways that cooperate to receive a locking portion of a line such as a suture in such a manner that the locking portion can only be drawn through the passageways along one direction. A second suture locking portion may also received by the passageways, or by one of the two passageways in combination with a third passageway. The body may have an elongated, compact shape that is easily implantable in the body.

18 Claims, 23 Drawing Sheets

Related U.S. Application Data filed on Sep. 7, 2004, now Pat. No. 7,566,339, and a continuation-in-part of application No. 10/942,275, filed on Sep. 15, 2004, now Pat. No. 7,806,909, and a continuation-in-part of application No. 11/001,866, filed on Dec. 1, 2004, now Pat. No. 7,594,923.

(56) References Cited

U.S. PATENT DOCUMENTS

| | | |
|---|---|---|
| 4,646,394 A | 3/1987 | Krauss |
| 4,785,509 A | 11/1988 | Fisher |
| 4,831,692 A | 5/1989 | Chuan |
| 4,910,834 A | 3/1990 | Minkler |
| 4,932,962 A | 6/1990 | Yoon et al. |
| 4,976,013 A | 12/1990 | Wax |
| 5,037,439 A | 8/1991 | Albrektsson et al. |
| 5,074,874 A | 12/1991 | Yoon et al. |
| 5,123,913 A | 6/1992 | Wilk et al. |
| 5,139,520 A | 8/1992 | Rosenberg |
| 5,284,485 A | 2/1994 | Kammerer et al. |
| 5,306,301 A | 4/1994 | Graf et al. |
| 5,374,269 A | 12/1994 | Rosenberg |
| D356,154 S | 3/1995 | Ferragamo |
| 5,403,330 A | 4/1995 | Tuason |
| 5,445,167 A | 8/1995 | Yoon et al. |
| 5,456,721 A | 10/1995 | Legrand |
| 5,464,427 A | 11/1995 | Curtis |
| 5,527,341 A | 6/1996 | Gogolewski et al. |
| 5,572,770 A | 11/1996 | Boden |
| 5,584,835 A | 12/1996 | Greenfield |
| 5,601,557 A | 2/1997 | Hayhurst |
| 5,607,430 A | 3/1997 | Bailey |
| 5,630,824 A | 5/1997 | Hart |
| 5,632,745 A | 5/1997 | Schwartz |
| 5,645,588 A | 7/1997 | Graf et al. |
| 5,653,719 A | 8/1997 | Raiken |
| 5,693,060 A | 12/1997 | Martin |
| 5,725,556 A | 3/1998 | Moser et al. |
| 5,741,281 A | 4/1998 | Martin |
| 5,741,301 A | 4/1998 | Pagedas |
| 5,752,964 A | 5/1998 | Mericle |
| 5,759,189 A | 6/1998 | Ferragamo et al. |
| 5,766,250 A | 6/1998 | Chervitz et al. |
| 5,769,894 A | 6/1998 | Ferragamo |
| 5,769,899 A | 6/1998 | Schwartz et al. |
| 5,782,864 A | 7/1998 | Lizardi |
| 5,839,768 A | 11/1998 | Wackerly |
| 5,891,168 A | 4/1999 | Thal |
| 5,931,855 A | 8/1999 | Buncke |
| 5,950,284 A | 9/1999 | Persson |
| 6,024,758 A | 2/2000 | Thal |
| 6,030,007 A | 2/2000 | Bassily et al. |
| 6,045,574 A | 4/2000 | Thal |
| 6,063,106 A | 5/2000 | Gibson |
| 6,066,160 A | 5/2000 | Colvin et al. |
| 6,068,648 A | 5/2000 | Cole et al. |
| 6,093,201 A | 7/2000 | Cooper |
| 6,095,282 A | 8/2000 | Sadeck |
| 6,099,568 A | 8/2000 | Simonian et al. |
| 6,106,545 A | 8/2000 | Egan |
| 6,117,161 A | 9/2000 | Li |
| 6,132,439 A | 10/2000 | Kontos |
| 6,171,317 B1 | 1/2001 | Jackson et al. |
| 6,171,342 B1 | 1/2001 | O'Neil et al. |
| 6,235,057 B1 | 5/2001 | Roger et al. |
| 6,283,996 B1 | 9/2001 | Chervitz et al. |
| 6,319,271 B1 | 11/2001 | Schwartz et al. |
| 6,371,958 B1 | 4/2002 | Overaker |
| 6,432,123 B2 | 8/2002 | Schwartz et al. |
| 6,485,065 B2 | 11/2002 | Lusk et al. |
| 6,514,274 B1 | 2/2003 | Boucher |
| 6,533,802 B2 | 3/2003 | Bojarski et al. |
| 6,544,267 B1 | 4/2003 | Cole et al. |
| 6,562,071 B2 | 5/2003 | Jarvinen |
| 6,575,986 B2 | 6/2003 | Overaker |
| 6,652,561 B1 | 11/2003 | Tran |
| 6,743,232 B2 | 6/2004 | Overaker et al. |
| 6,749,616 B1 | 6/2004 | Nath |
| 6,770,076 B2 | 8/2004 | Foerster |
| 6,902,573 B2 | 6/2005 | Strobel |
| 7,338,492 B2 | 3/2008 | Singhatat |
| 7,455,683 B2 | 11/2008 | Geissler |
| 7,537,604 B2 | 5/2009 | Huebner |
| 7,572,275 B2 | 8/2009 | Fallin |
| 7,722,644 B2 * | 5/2010 | Fallin et al. .................. 606/232 |
| 7,731,718 B2 | 6/2010 | Schwammberger |
| D626,231 S | 10/2010 | Perchik |
| 7,846,180 B2 | 12/2010 | Cerier |
| 7,862,597 B2 | 1/2011 | Gause |
| 7,867,253 B2 | 1/2011 | McMichael |
| 7,875,057 B2 | 1/2011 | Cook |
| 7,875,058 B2 | 1/2011 | Holmes, Jr. |
| 7,931,680 B2 | 4/2011 | Myerson |
| 7,955,388 B2 | 6/2011 | Jensen |
| 8,062,334 B2 | 11/2011 | Green |
| 8,128,652 B2 | 3/2012 | Paprocki |
| 8,277,484 B2 | 10/2012 | Barbieri |
| 2002/0019649 A1 | 2/2002 | Sikora |
| 2002/0120274 A1 | 8/2002 | Overaker et al. |
| 2002/0120281 A1 | 8/2002 | Overaker et al. |
| 2002/0123758 A1 | 9/2002 | Bachman et al. |
| 2003/0225456 A1 | 12/2003 | Ek |
| 2004/0015171 A1 | 1/2004 | Bojarski et al. |
| 2004/0098053 A1 | 5/2004 | Tran |
| 2004/0133217 A1 | 7/2004 | Watschke |
| 2004/0133238 A1 | 7/2004 | Cerier |
| 2004/0133239 A1 | 7/2004 | Singhatat |
| 2004/0138683 A1 | 7/2004 | Shelton et al. |
| 2004/0138706 A1 | 7/2004 | Abrams et al. |
| 2004/0153103 A1 | 8/2004 | Schwartz et al. |
| 2004/0243180 A1 | 12/2004 | Donnelly |
| 2006/0265064 A1 | 11/2006 | Re |
| 2006/0293709 A1 | 12/2006 | Bojarski |
| 2007/0225805 A1 | 9/2007 | Schmieding |
| 2007/0233241 A1 | 10/2007 | Graf et al. |
| 2008/0177302 A1 | 7/2008 | Shurnas |
| 2008/0234819 A1 | 9/2008 | Schmieding |
| 2009/0204146 A1 | 8/2009 | Kaiser |
| 2010/0125297 A1 | 5/2010 | Guederian |
| 2010/0204731 A1 | 8/2010 | Hart |
| 2010/0256677 A1 | 10/2010 | Albertorio |
| 2010/0262185 A1 | 10/2010 | Gelfand |
| 2011/0046734 A1 | 2/2011 | Tobis |
| 2012/0078299 A1 | 3/2012 | Ramos |
| 2012/0083837 A1 | 4/2012 | Ferragamo |
| 2012/0123474 A1 | 5/2012 | Zajac |
| 2012/0123541 A1 | 5/2012 | Albertorio |
| 2012/0130492 A1 | 5/2012 | Eggli |
| 2012/0283830 A1 | 11/2012 | Myers |

FOREIGN PATENT DOCUMENTS

WO    WO2004062506 A1    7/2004

\* cited by examiner

COMPACT LINE LOCKS AND METHODS

CROSS-REFERENCE TO RELATED APPLICATIONS

This application is a Continuation of the following, which is herein incorporated by reference:

U.S. application Ser. No. 11/125,885 filed May 9, 2005, which carries Applicants' now U.S. Pat. No. 7,722,644, and is entitled COMPACT LINE LOCKS AND METHODS, which is a C.I.P. of the following, all of which are incorporated herein by reference:

U.S. application Ser. No. 10/459,375, filed Jun. 11, 2003, which carries Applicants' now U.S. Pat. No. 7,150,757, and is entitled LINE LOCK SUTURE ATTACHMENT SYSTEMS AND METHODS;

U.S. application Ser. No. 10/936,376, filed Sep. 7, 2004, which carries Applicants' now U.S. Pat. No. 7,566,339, and is entitled ADJUSTABLE LINE LOCKS AND METHODS;

U.S. application Ser. No. 10/942,275, filed Sep. 15, 2004, which carries Applicants' now U.S. Pat. No. 7,806,909, and is entitled LINE LOCK THREADING SYSTEMS AND METHODS; and U.S. application Ser. No. 11/001,866, filed Dec. 1, 2004, which carries Applicants' now U.S. Pat. No. 7,594,923, and is entitled LINE LOCK SUTURE ATTACHMENT SYSTEMS AND METHODS.

BACKGROUND OF THE INVENTION

1. The Field of the Invention

The present invention relates generally to devices to replace knots and more specifically to devices to replace surgical knots tied in open, arthroscopic, and endoscopic procedures.

2. The Relevant Technology

Numerous devices have been developed to eliminate the need to tie knots as a way of securing a line. The devices that accomplish the same function as a knot, which is in part to secure a line to retain tension in a portion of the line, are typically referred to as line locks.

Line locks generally operate in one of two ways. Some line locks are manually actuated to secure one or more lines so that tension is maintained in a portion of the line(s). Once actuated, the line lock resists sliding along the line(s) either toward or away from the tensioned portion of the line. Other line locks are continuously adjustable in one direction so that tension is increased in the portion of the line upon which the line lock is advanced. The continuously adjustable line locks resist movement away from the tensioned portion of the line, but can be further advanced toward the tensioned portion of the line with an appropriately applied force.

The portion of a line that is put under tension, typically to secure some object, is commonly referred to as the standing end. The portion of the line that extends toward the line handler is commonly referred to as the working end. A knot in a line, or a line lock attached to a line, is the demarcation between the standing end and the working end.

Continuously adjustable line locks offer several advantages. They are passive locking devices, meaning that no other operation is required to secure the line lock once it is moved along the line to its desired position. Furthermore, these line locks can be used to continuously increase the tension in the standing end until it reaches a desired level of tension.

The advantages of line locks over tied knots are very attractive in many varied applications, including the use of surgical sutures. However, the line locks developed to date have many deficiencies when considered for surgical suture applications. For example, known line locks use line on line friction to create the locking effect, and this line on line friction makes it difficult to advance the line lock over suture. Known line locks rely on maintenance of tension in the standing end to prevent the line lock from migrating back along the working end.

In surgical suture applications, the working end is typically trimmed closely to the line lock. As a result, the line lock can easily disassociate from the suture once tension in the standing end is lost. In most, if not all, surgical applications, a free-floating device such as a line lock can potentially harm adjacent body tissues. Additionally, known line locks are susceptible to loosening during cyclic variations in the tension of the standing end. This cyclic variation in the standing end tension is common in surgical applications as tissues are stressed and then relaxed. Loosening of the line lock thus compromises the securing function for which it was intended. Furthermore, known line locks are often somewhat bulky, and are therefore not optimally designed for implantation in the body.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to line locks that can be used in part to replace surgical knots tied in sutures in open, arthroscopic, and endoscopic procedures. By increasing the size of the line locks, it is also appreciated that the line locks can be used outside of surgical procedures for any use where it is desired to selectively adjust and/or tie off a line such as a rope, cord, string, or other conventional type of line.

In this application, the term "couple" broadly refers to connection of two items to each other. Two items may be "coupled" if they are connected together in a manner that prevents relative motion on one direction, but not another. A "longitudinal length" of an object is the length of the object along its longest dimension. "Cooperation" of a plurality of passageways to receive multiple suture portions does not require that each suture portion pass through all of the cooperating passageways.

Figure 1:
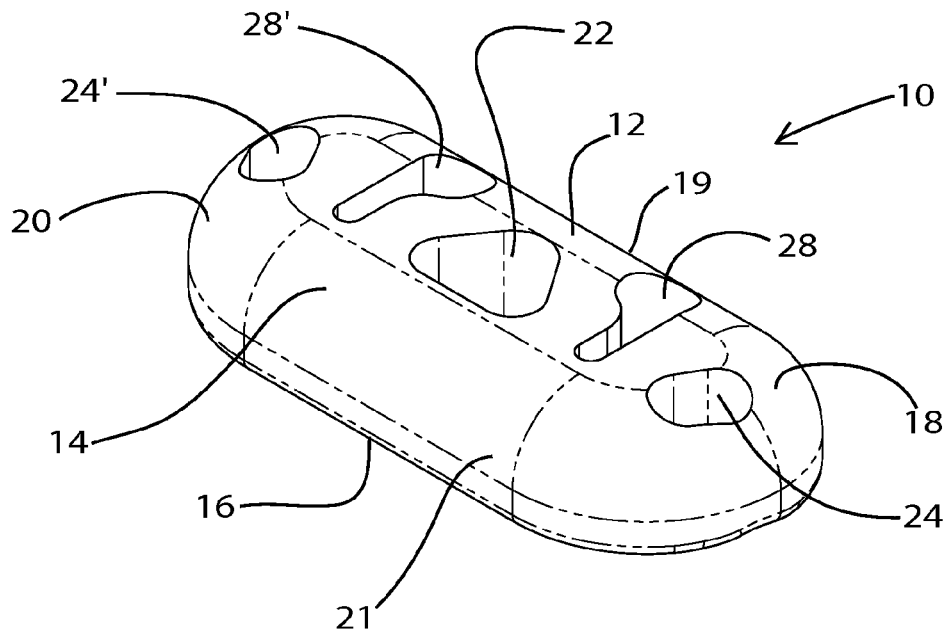
FIG. 1 is a perspective view of an adjustable line lock.

Depicted in FIG. 1 is one embodiment of a line lock 10 incorporating features of the present invention. Line lock 10 comprises an elongated body 12 having a top surface 14 and an opposing bottom surface 16 that each extend between a first end 18 and an opposing second end 20. Body 12 also has a first side 19 and an opposing second side 21 extending between first end 18 and second end 20. In the embodiment depicted, body 12 has a substantially rectangular configuration with rounded ends. As will be apparent from the following disclosure, however, body 12 can be any desired configuration such as triangular, circular, square or any other polygonal or irregular configuration.

In typical surgical applications, body 12 has a maximum dimension D along its length (FIG. 2) which is typically less than about 2 cm, more commonly less than about 1.5 cm, and even more commonly less than about 1 cm. Other dimensions can also be used. By way of example and not by limitation, in one embodiment body 12 has a height in a range between about 1 mm to about 1.5 mm, a width in a range between about 2 mm to about 3 mm, and length D in a range between about 5 mm to about 8 mm. In non-surgical applications, body 12 can be any desired dimension. For example, maximum dimension D can be in a range from about 5 cm to about 0.5 m. Again, other dimensions can also be used.

For use in surgical applications, body 12 can be comprised of any biocompatible material. The biocompatible material can be bioabsorbable or non-bioabsorbable. Examples of typical materials include non-bioabsorbable plastic, bioabsorbable plastic, synthetic tissue, and allograft tissue. In non-surgical applications, body 12 can be made of any desired material such as metal, plastic, wood, fiberglass, composite, or the like.

As depicted in FIG. 1, centrally extending through body 10 between top surface 14 and bottom surface 16 is a primary passageway 22. As used in the specification and appended claims, the term "passageway" is broadly intended to include closed apertures, such as depicted by primary passageway 22, partially bounded apertures, open channels, recesses, grooves, slots, and the like, that are capable of receiving a line and at least partially retaining the line therein. The term "line" as used in the specification and appended claims is broadly intended to include suture, cord, rope, filament, wire, cable, and any other form of line.

In this application, the phrase "substantially bounded aperture" refers to an aperture that is sufficiently encircled by material to prevent a line from exiting the aperture via motion transverse to the length or axis of the aperture. Thus, a substantially bounded aperture may be fully encircled by material, or may have one or more breaks, each of which is smaller than the diameter of the line that is to pass through the substantially bounded aperture.

Extending between surfaces 14 and 16 at first end 18 of body 12 is a first secondary passageway 24. A second secondary passageway 24' extends between surfaces 14 and 16 at second end 20. Extending through body 12 at a location between primary passageway 22 and first secondary passageway 24 is a first working passageway 28. In one embodiment, although not necessarily required, first working passageway 28 is disposed between primary passageway 22 and first secondary passageway 24 such that a geometric line segment 36 (FIG. 2) can be extended between primary passageway 22 and first secondary passageway 24 so that line segment 36 intersects with first working passageway 28. Similar to first working passageway 28, a second working passageway 28' extends through body 12 at a location between primary passageway 22 and second secondary passageway 24'.

Each working passageway 28 and 28' has an elongated transverse cross sectional area that extends between a first end 38 and an opposing second end 40. Each working passageway 28, 28' comprises an enlarged access region 32 at first end 38 which communicates with a constricted capture slot 34 at second end 40. Access region 32 is sized to enable easy feeding of a line into and through the corresponding working passageways 28, 28'. Accordingly, although access region 32 can be slightly smaller than the transverse cross sectional area of the line which is to be passed therethrough, access region 32 typically has a transverse cross sectional area that is equal to or slightly larger than the transverse cross sectional area of the line that is to be passed therethrough.

In contrast, capture slot 34 has a width W that is substantially equal to or less than the diameter of the line that is to be passed through working passageways 28, 28'. For example, in one embodiment width W is less than about 0.9 times the diameter of the line and more commonly less than about 0.75 times the diameter of the line. It is appreciated that working passageways 28, 28' can come in a variety of different configurations. For example, capture slot 34 can come in a variety of different constricted, tapered, or notched shaped configurations that are capable of securely retaining a line through wedged engagement. For line made of less compressible material, such as metal, the required difference between the width W and the diameter of the line may be less than the examples given above.

Figure 2:
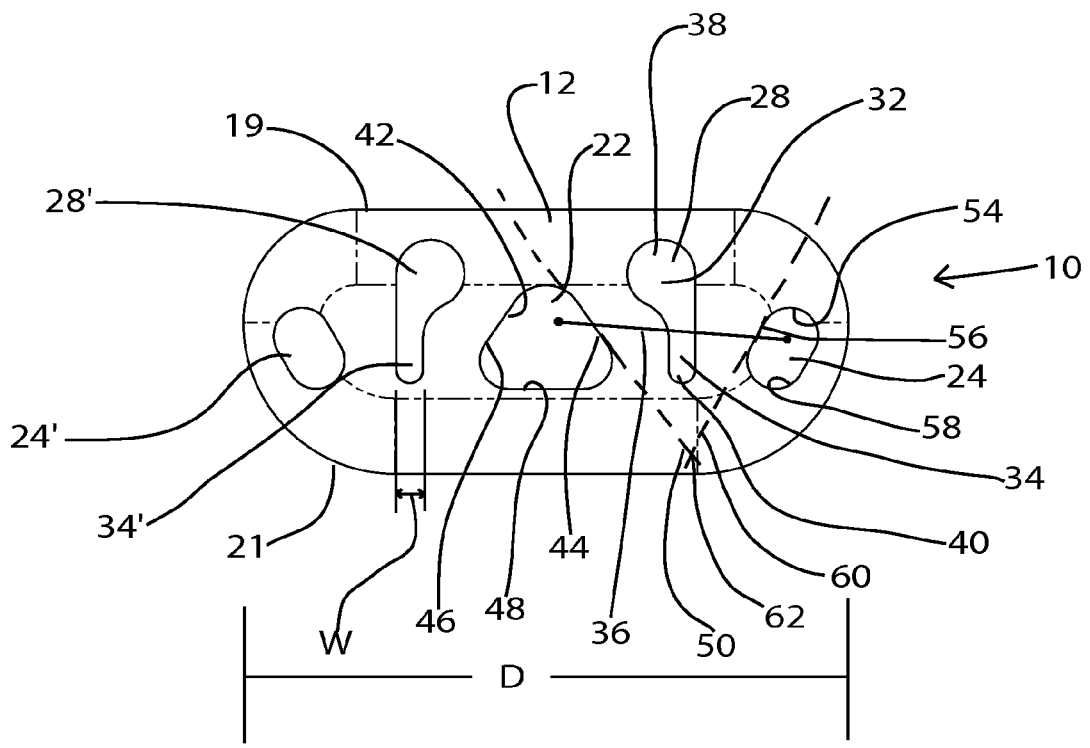
FIG. 2 is a top plan view of line lock shown in FIG. 1.

As depicted in FIG. 2, central passageway 22 is bounded by an interior surface 42 of body 12 having a substantially triangular transverse cross section. Interior surface 42 comprises a first side face 44 disposed toward first working passageway 28, a second side face 46 disposed toward second working passageway 28' and which intersects with first side face 44, and a third side face 48 extending between first side face 44 and second side face 46. Although side faces 44 and 46 are shown as being substantially flat, in alternative embodiments side faces 44 and 46 can be curved or irregular. In one embodiment, however, first side face 44 is substantially disposed in or tangent to a first plane illustrated by dashed line 50. With reference to FIG. 2, plane 50 slopes toward second end 40 of first working passageway 28 as plane 50 extends from first side 19 of body 12 to second side 21.

First secondary passageway 24 is bounded by an interior surface 54 of body 12 having an elongated transverse cross section. Interior surface 54 comprises a first side face 56 disposed toward first working passageway 28 and an opposing second side face 58. Although side faces 56 and 58 are shown as being substantially flat, in alternative embodiments side faces 56 and 58 can also be curved or irregular. Again, in one embodiment first side face 56 is substantially disposed in or tangent to a second plane illustrated by dashed line 60. With reference to FIG. 2, second plane 60 slopes toward second end 40 of first working passageway 28 as second plane 60 extends from first side 19 of body 12 to second side 21.

In the above discussed configuration, first plane 50 and second plane 60 are disposed so as to be converging as they extend from first side 19 of body 12 to second side 21. In the embodiment depicted, planes 50 and 60 intersect at a location 62 on body 12 that is at least substantially aligned with a central longitudinal axis of capture slot 34. In other embodiments, location 62 can be directly adjacent to body 12 or at a distance from body 12. Likewise, location 62 need not be aligned with the central longitudinal axis of capture slot 34. Although not required, in one embodiment planes 50 and 60 are disposed at equally opposing angles relative to the central longitudinal axis of capture slot 34. Furthermore, planes 50 and 60 can intersect so as to form an inside angle therebetween in a range between about 5° to about 85°.

Second secondary passageway 24' has substantially the same configuration as first secondary passageway 24. Likewise, second secondary passageway 24' has substantially the same relative position to second working passageway 28' and second side face 46 of primary passageway 22 as first secondary passageway 26 has to first working passageway 28 and first side face 44 of primary passageway 22. As such, the discussion with regard to planes 50 and 60 are also applicable to primary passageway 22 and second secondary passageway 24'.

By way of example of the passageways and not by limitation, for use with a size USP #2 braided suture, which has a diameter in a range between about 0.5 mm to about 0.6 mm, primary passageway 22 has a length in a range between about 1.3 mm to about 1.5 mm and a width in a range between about 1 mm to about 1.3 mm. Secondary passageways 24 and 24' have a width of about 0.8 mm and a length in a range between 1 mm to about 1.3 mm. Access region 32 of working passageways 28 and 28' have width in a range between about 0.7 mm to 1 mm while capture slots 17 have a width in a range between about 0.3 mm to 0.4 mm.

Figure 3:
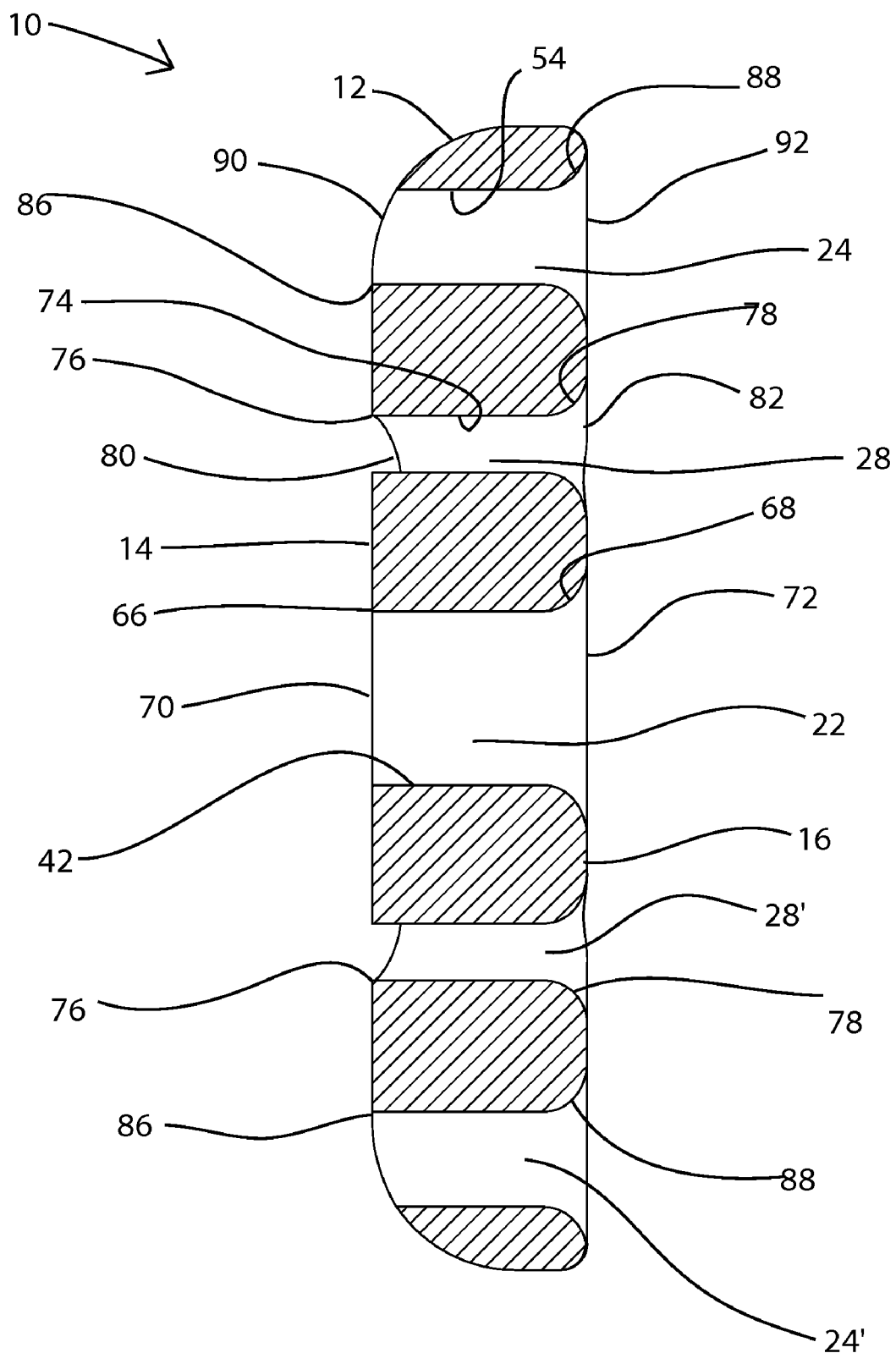
FIG. 3 is an elevated cross sectional side view of the line lock shown in FIG. 1.

Depicted in FIG. 3, interior surface 42 of primary passageway 22 extends to a top outside corner 66 and an opposing bottom outside corner 68. Top outside corner 66 bounds a top primary opening 70 while bottom outside corner 66 bounds a bottom primary opening 72. Similarly, first working passageway 28 has an interior surface 74 that extends to a top outside corner 76 and an opposing bottom outside corner 78. Top outside corner 76 bounds a top working opening 80 while bottom outside corner 76 bounds a bottom working opening 82. Likewise, interior surface 54 of first secondary passageway 24 extends to a top outside corner 86 and an opposing bottom outside corner 88. Top outside corner 86 bounds a top secondary opening 90 while bottom outside corner 86 bounds a bottom secondary opening 92.

For reasons as will be discussed below in greater detail, each of top outside corners 66, 76, and 86 has a radius of curvature that is smaller than the radius of curvature of the corresponding bottom outside corners 68, 78, 88. By way of example and not by limitation, in one embodiment top outside corners 66, 76, and 86 each have a radius of curvature in a range between about 0 mm to about 1 mm with about 0 mm to about 0.5 mm being more common. In contrast, bottom outside corners 68, 78, and 88 each have a radius of curvature in a range between about 0.25 mm to about 2 mm with about 0.5 mm to about 1.5 mm being more common. Other dimensions can also be used, particularly outside of the surgical area. In yet other embodiments it is appreciated that the top outside corners and the bottom outside corners can have the same radius of curvature or that only one or more of the top outside corners may be smaller than one or more of the bottom outside corners. In still other embodiments, it is appreciated that only a portion of one or more of the top outside corners may be smaller than a portion of one or more of the bottom outside corners.

It is again noted that second secondary passageway 24' and second working passageway 28' having substantially the same configuration as first secondary passageway 24 and first working passageway 28, respectively. As such, the same discussion with regard to the outside corners are also applicable thereto. Likewise, like elements are identified by like reference characters.

Figure 4A:
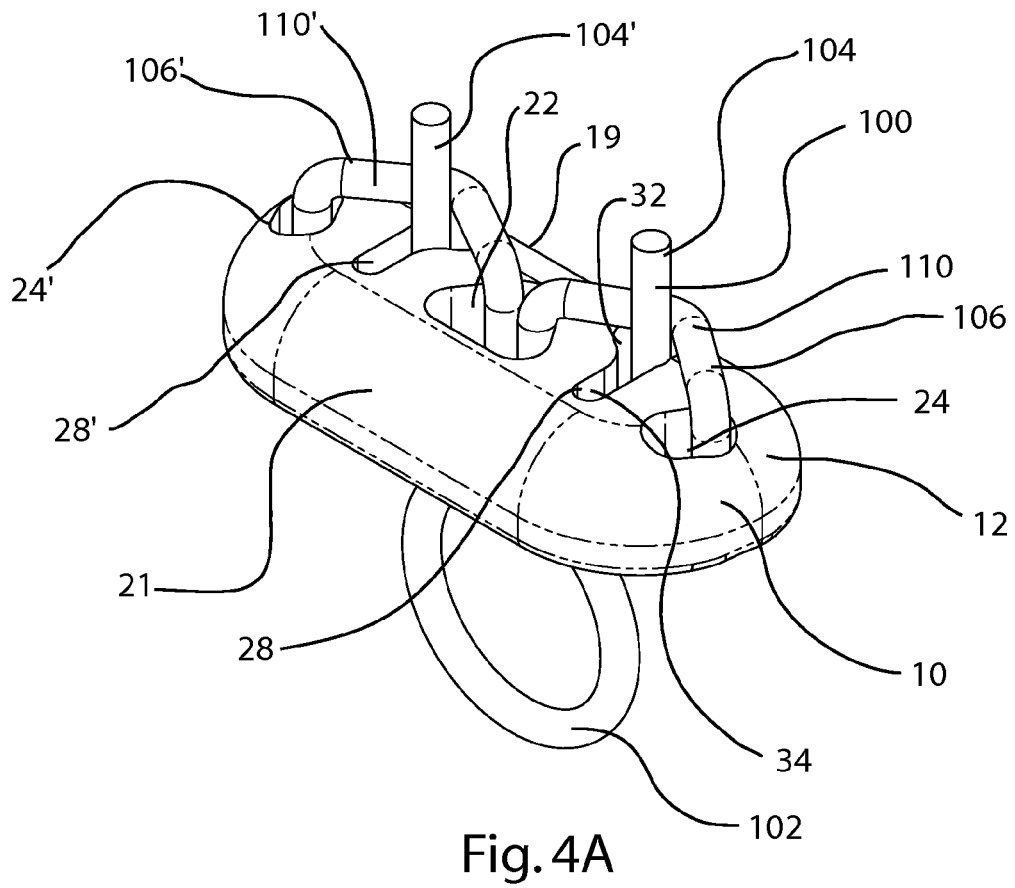
FIG. 4A is a perspective view of the line lock shown in FIG. 1 with a line routed therethrough in a slack unlocked position.

Depicted in FIG. 4A is a line 100 adjustably mounted on line lock 12. Line 100 comprises a standing portion 102 in the form of a loop which extends below primary passageway 22, a first working portion 104 which extends out of first working passageway 28, and a first locking portion 106 extending therebetween. It is appreciated that each of the sections 102, 104, and 106 of line 100 are relative to each other in that they change as line 100 is adjusted on line lock 10. Line 100 further includes a second working portion 104' which extends out of second working passageway 28' and a second locking portion 106' that extends between standing portion 102 and second working portion 104'.

First locking portion 106 extends up through primary passageway 22, down through first secondary passageway 24, and then up through first working passageway 28. The section of locking portion 106 extending between primary passageway 22 and first secondary passageway 24 is referred to as compression section 110. Line 100 passes up through first working passageway 28 so that first working portion 104 is disposed between compression section 110 and capture slot 34. Second locking portion 106' is similarly passed through passageways 22, 24', and 28'.

During use, standing portion 102 of line 100 is typically looped around, embedded within, or passed through tissue, or some other structure. To secure standing portion 102 to the structure, unwanted slack is removed from standing portion 102. This is accomplished by sliding line lock 10 over standing portion 102 and/or pulling on working portion 104 and/or 104' so that the unwanted slack is pulled through line lock 10. In either event, at least one of working portions 104 and 104' increases in length while standing portion 102 shortens.

In the configuration depicted in FIG. 4A, line 100 is passing through enlarged access regions 32 of working passageways 28 and 28'. In this position, relative locking portions 106 and 106' freely slide through corresponding passageways of line lock 10 as the unwanted slack from standing portion 102 is removed. A mild tension force is typically applied to working portions 104 and 104' as the unwanted slack is removed. The applied force pushes compression section 110 and 110' back toward first side 19 of body 12 and thus away from capture slots 34, 34'. In turn, the portion of line 100 passing through primary passageway 22 and secondary passageways 24 and 24' also naturally slides back within the passageways toward first side 19 of body 12. This movement of line 100 helps to decrease frictional resistance on line 100.

Figure 4B:
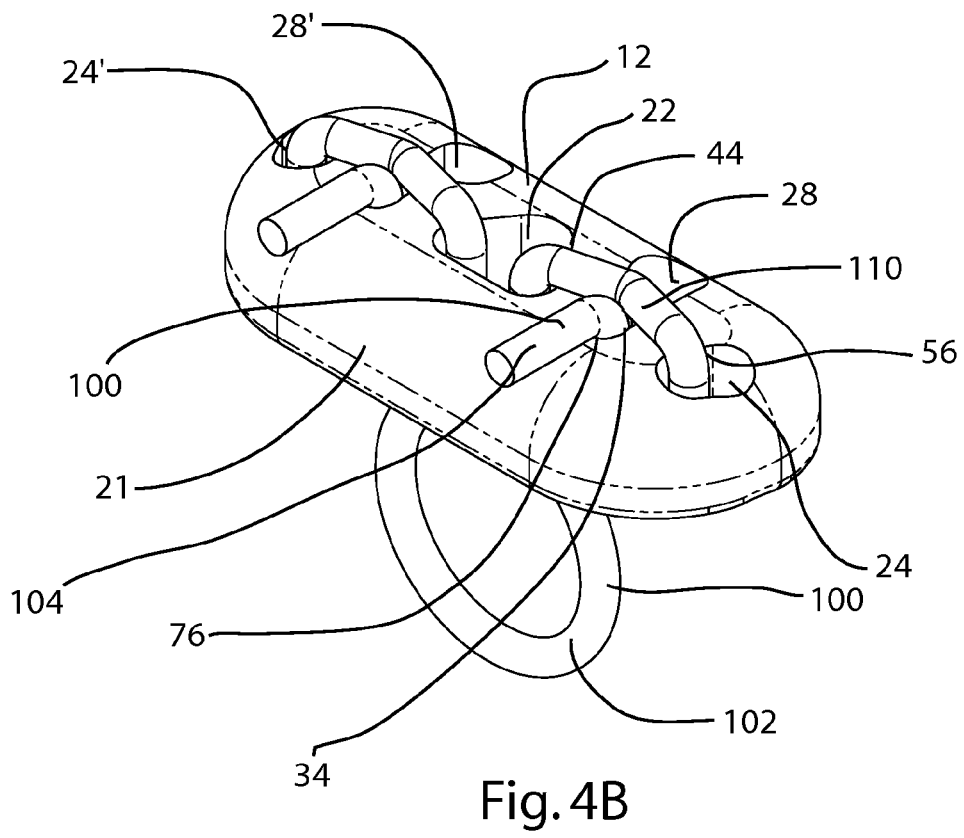
FIG. 4B is a perspective view of the line lock shown in FIG. 4A with the line in a tensioned locked position.

Once the slack is removed from standing portion 102, further force is applied to working portions 104, 104' and/or line lock 10 so as to tension locking portions 106, 106' on line lock 10. As depicted in FIG. 4B, as line 100 is tensioned, the diverging side face 44 of primary passageway 22 and side face 56 of first secondary passageway 24 cause the portions of line 100 passing therethrough, and thus compression portion 110 extending therebetween, to slide toward first side 21 of body 12.

Furthermore, as line 100 is tensioned, compression portions 110, 110' are shortened causing them to move into a more linear orientation. As a result of the above, tensioning of line 100 causes compression portions 110, 110' to force working portions 104, 104' toward corresponding capture slots 34, 34'. In turn, at least a portion of line 100 within working passageways 28 and 28' is forced into corresponding capture slots 34, 34' so that line 100 is secured therein by wedged frictional engagement. That is, line 100 is secured by compression within capture slots 34, 34' because line 100 has a diameter larger than the width of capture slots 34, 34'. Once line 100 is captured under compression in capture slots 34, 34', line 100 will remain captured even if there is a complete loss of tension in standing end 102. Thus, "locking" of line lock 10 to line 100 ensures that line lock 10 will not become separated from line 100, even under cyclic changes in line tension in standing end 102. Furthermore, line lock 10 is continuously adjustable in that further tension can be applied to standing portions 104 and/or at any time to remove additional slack from standing portion 102 while retaining line 100 locked to line lock 10.

The passageways extending through line lock 10 are also configured such that as compression portions 110 and 110' force line 100 into capture slots 34 and 34', compression portions 110 and 110' also fold and/or bias working ends 104 and 104' over and/or against top outside corner 76 of capture slots 34 and 34'. In view of the relatively small radius of curvature of top outside corner 76, the engagement between the captured working ends 104 and 104' and top outside corner 76 creates a high degree of friction which forms a secondary locking mechanism between line 100 and line lock 10. As such, the engagement between capture working ends 104 and 104' and top outside corner 76 prevents backward movement of line lock 10 relative to line 100.

In the embodiment depicted in FIG. 4B, compression portion 110 is disposed above a portion of top outside corner 76 so as to directly bias working ends 104 against top outside corner 76. Compression portion 110 is also shown disposed directly above a portion of working end 104 that is biasing against top outside corner 76. In alternative embodiments, compression portion 110 when tensioned can extend between central passageway 22 and secondary passageways 24 without passing over working passageway 28. That is, compression portion 110 can pass at a location toward second side 21 of line lock 10 that is spaced apart from working passageway 28. In this embodiment, compression portion 110 still passes over working end 104, thereby remotely causing working end 104 to fold over and bias against top outside corner 76.

One of the unique features of the present embodiment is that as line lock 10 is advanced toward standing end 102 when standing end 102 is not under tension, i.e., when slack is being removed from standing end 102, working ends 104 and 104' tend to push away compression portions 110 and 110', as discussed above, thereby minimizing frictional engagement between working ends 104, 104', compression portions 110, 110' and line lock 10. As a result, line lock 10 can be easily advanced on line 100.

Furthermore, unlike some other continuously adjustable line locks known in the art that use a loop portion to draw in and wedge a portion of a line within a bore hole, compression portions 110 and 110' traverse a substantially straight path because they are constrained by secondary passageways 24 and 24' and primary passageway 22. This substantially straight path translates to a lower frictional resistance to sliding not possible with other adjustable line locks known in the art.

As previously discussed, line 100 is routed through passageways 22, 24, and 28 so as to pass over the outside corners of the passageways. When a tensioned section of line 100 passes around a first outside corner of line lock 10, friction produced between line 100 and the corresponding outside corner cause a decrease in tension on the portion of line 100 extending away from the outside corner on the side opposite the tensioned section. The friction produced at the outside corner must be overcome in order to cause line 100 to slide. Similarly, as the line passes around subsequent outside corners away from the tensioned section, each subsequent corner produces an incremental decrease in line tension and a corresponding incremental increase in friction that must be overcome to cause line 100 to slide. The loss in tension and increase in friction diminishes for each subsequent corner. Thus, the first corners are the most significant.

Figure 6:
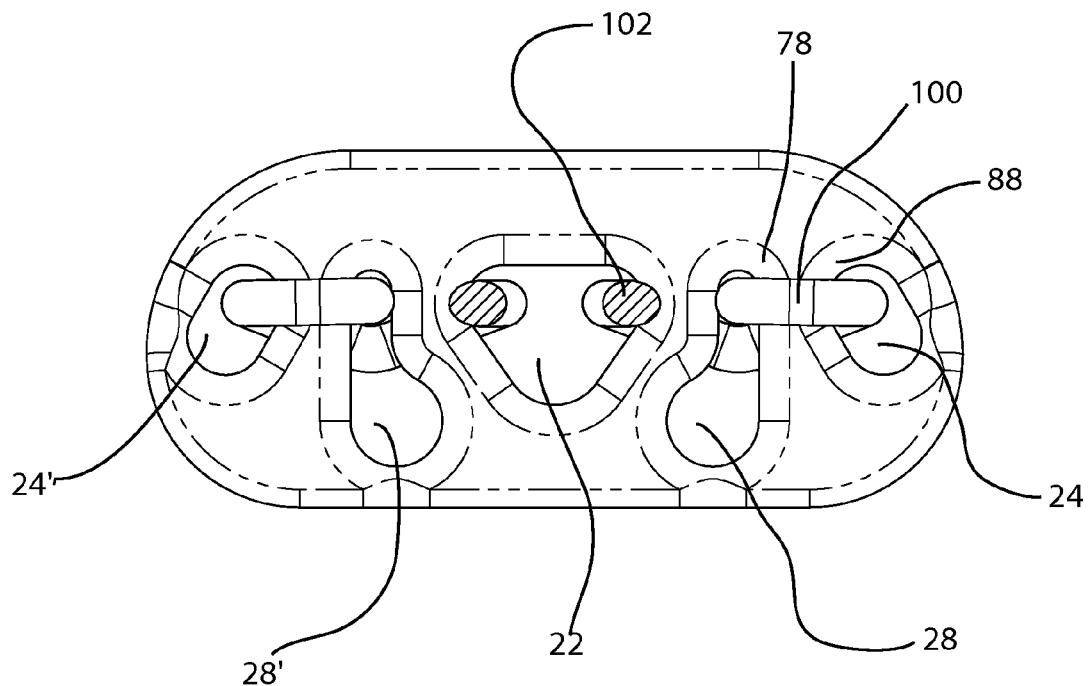
FIG. 6 is a bottom plan view of the line lock shown in FIG. 4B.

As depicted in FIG. 6, in view of the above discussion, when working end 104 is tensioned and standing end 102 is slack, line 100 extending from working end 104 toward line lock 10 first turns on bottom outside corner 78 of working passageway 28 and bottom outside corner 88 of secondary passageway 24. As a result of the fact that these are the closest outside corners to tensioned working end 104, outside corners 78 and 88 will produce the highest frictional resistance. Accordingly, to minimize the frictional resistance produced by outside corners 78 and 88 and thereby ease the sliding of line lock 10 toward standing end 102, outside corners 78 and 88 are generously rounded as previously discussed.

Figure 5:
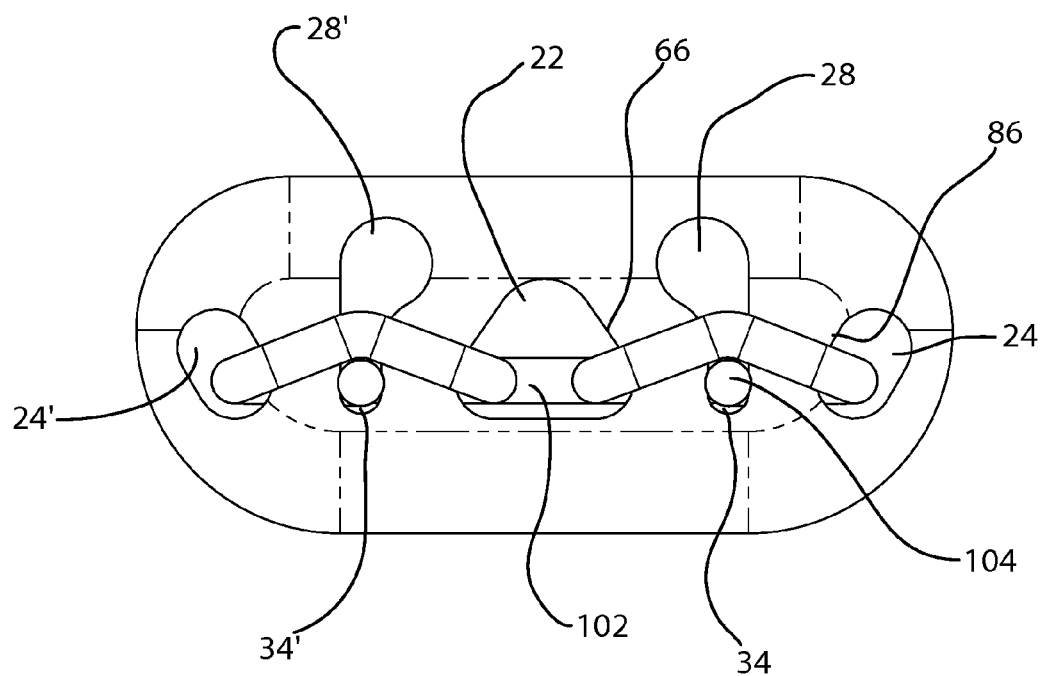
FIG. 5 is a top plan view of the line lock shown in FIG. 4B.

In contrast, as depicted in FIG. 5, when standing end 102 is tensioned and working end 104 is slack, line 100 extending from standing end 102 toward line lock 10 first turns on top outside corner 66 of primary passageway 22 and top outside corner 86 of secondary passageway 24. In view of the fact that these are the closest outside corners to tensioned standing end 102, outside corners 66 and 86 will produce the highest frictional resistance. Accordingly, to maximize the frictional resistance produced by outside corners 66 and 86 and thereby minimizing slipping of line 100 once tensioned, outside corners 66 and 86 are formed relative sharp as previously discussed. More specifically, top outside corners 66 and 86 have a smaller radius of curvature than bottom outside corners 78 and 88. It is noted that not all of each outside corner that bounds a corresponding opening has to have the same radius of curvature. For example, the portion of each outside corner that directly engages line 100 can have a radius of curvature that is different from the remainder of the corresponding outside corner.

Figure 7:
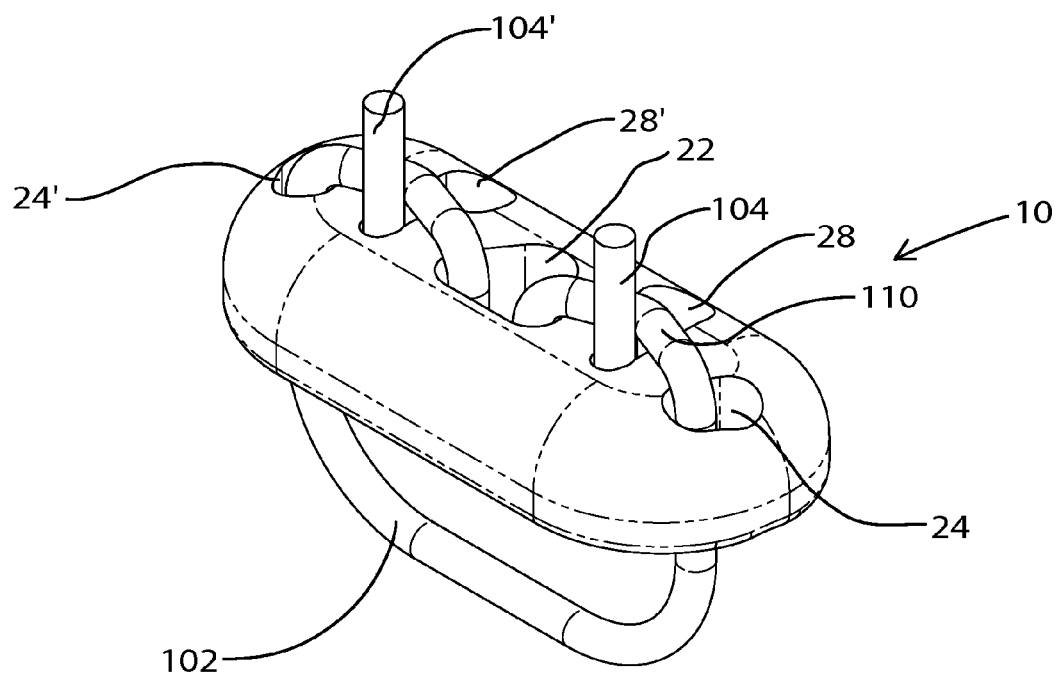
FIG. 7 is a perspective view of the line lock shown in FIG. 4A with the line routed in a different path.

Depicted in FIG. 7, line lock 10 is shown having an alternative routing of line 100. To achieve this routing, working ends 104 and 104' are passed up through secondary passageways 24 and 24', respectively, down through primary passageway 22, and then back up through working passageways 28 and 28', respectively. Again compression portions 110 and 110' are formed that selectively force working ends 104 and 104' toward capture slots 34 as discussed above. In yet another alternative, it is appreciated that one end of line 100 can be routed as shown in FIG. 4A while the opposing end of line 100 is routed as shown in FIG. 7.

Figure 8:
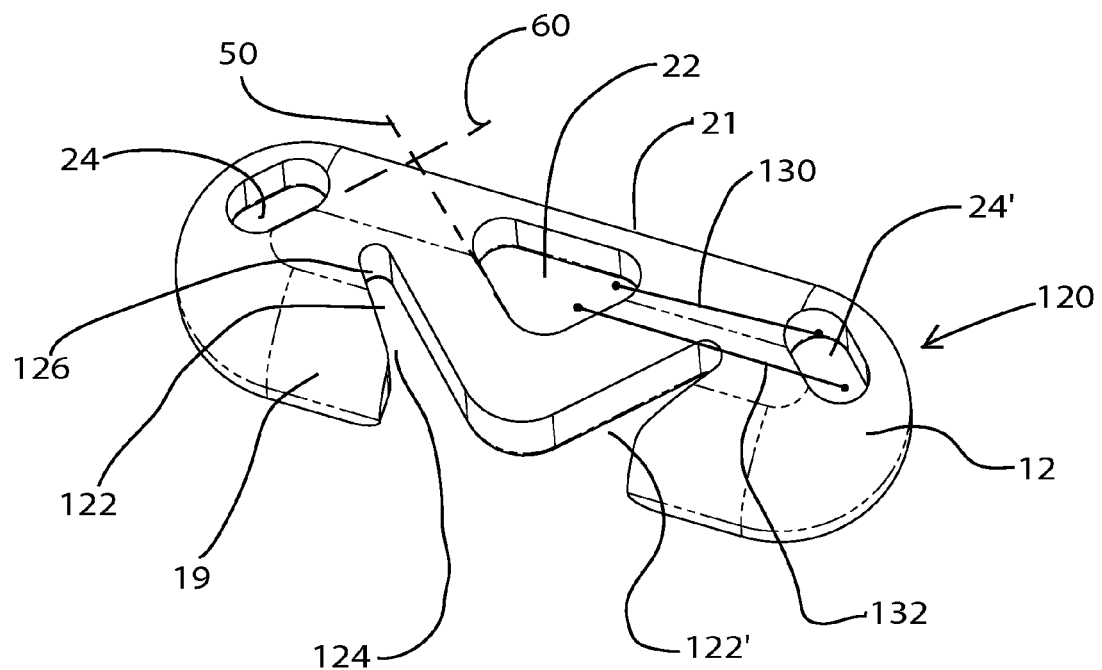
FIG. 8 is a perspective view of an alternative embodiment of the line lock shown in FIG. 1 with open working passageways.

Depicted in FIG. 8 is an alternative embodiment of a line lock 120. It is noted that all common elements of alternative embodiments of line locks disclosed herein are identified by like reference characters. Line lock 120 comprises body 12 having primary passageway 22 and secondary passageways 24 and 24' extending therethrough as discussed above with regard to FIG. 1. In contrast to the circumferentially closed working passageways 28, 28', however, line lock 120 comprises working passageways 122 and 122' that are circumferentially open. That is, each working passageway 122 and 122' comprises an elongated tapered slot having a first end 124 and an opposing second end 126. First end 124 is open along first side 19 of body 12 to facilitate convenient loading of line 100 therein. First end 124 also typically has a width greater than the diameter of line 100. Second end 126 extends to a location between primary passageway 22 and a corresponding one of secondary passageway 24, 24'.

In this embodiment it is noted that the passageways are positioned such that a geometric line segment 130 can be extended between primary passageway 22 and secondary passageway 24' such that line segment 130 does not intersect with working passageway 122'. However, a geometric line segment 132 can also be extended between primary passageway 22 and secondary passageway 24' such that line segment 132 intersects with working passageway 122'. Second end 126 of each working passageway 122, 122' typically has a width substantially equal to or smaller than the diameter of line 100.

Figure 9:
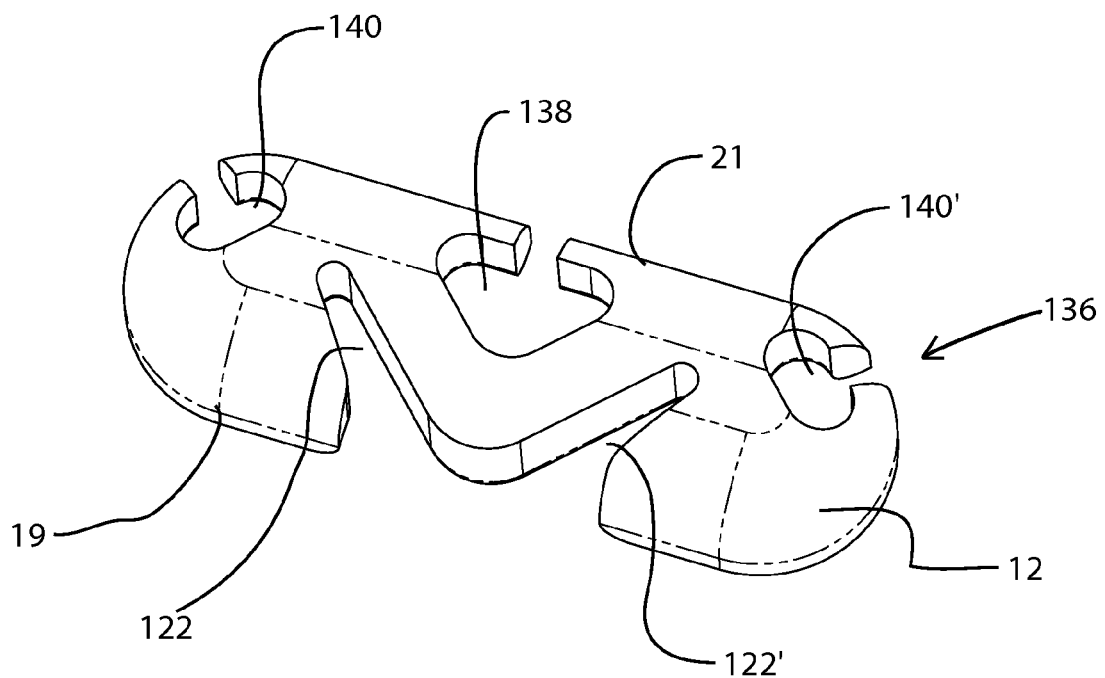
FIG. 9 is a perspective view of another alternative embodiment of the line lock shown in FIG. 1 with open passageways.

Depicted in FIG. 9 is another alternative embodiment of a line lock 136 having substantially the same configuration as line lock 120. In contrast to the circumferentially bounded primary passageway 22 and secondary passageways 24 and 24' of line lock 120 in FIG. 8, however, line lock 136 comprises a partially bounded primary passageway 138 which is open at second side 21 of body 12 and partially bounded secondary passageways 140 and 140' that are also each open at or adjacent to second side 21 of body 12.

Figure 10:
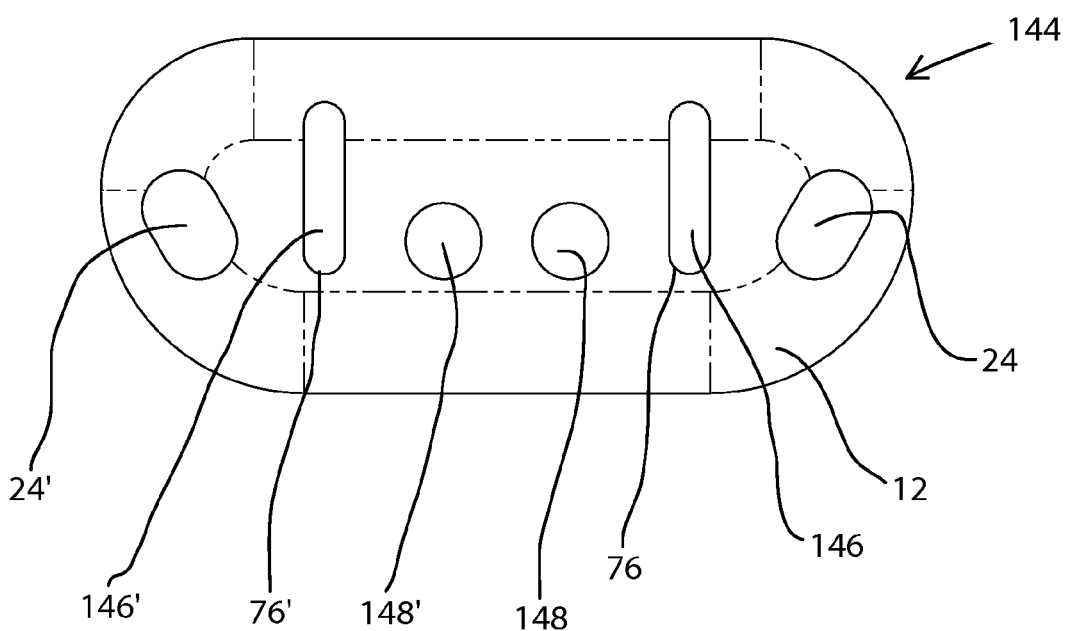
FIG. 10 is a perspective view of another alternative embodiment of the line lock shown in FIG. 1 with dual primary passageways and uniform working passageways.

Two separate locking features were previously discussed with regard to securing line 100 to line lock 10. Specifically, line 100 is secured by being wedged into capture slots 34 and 34' and by biasing working portions 104 and 104' against the top outside corner 76 of each working passageway 28, 28'. In alternative embodiments, it is appreciated that the locking features can be used independently. For example, depicted in FIG. 10 is a line lock 144 having body 12 with secondary passageways 24 and 24'. In contrast to line lock 10, however, line lock 144 comprises working passageways 146 and 146' wherein capture slots 34 have been eliminated. Working passageways 146 and 146' merely comprise elongated channels having a width substantially the same size or larger than the diameter of the line 100 to be passed therethrough. Line 100 is thus primarily secured to line lock 144 as a result of compression portions 110, 110' biasing line 100 against top outside corner 76 of each working passageways 146 and 146' as previously discussed.

Line lock 144 is also distinguished over line lock 10 in that primary passageway 22 has been replaced with a first primary passageway 148 and a spaced apart second primary passageway 148'. Primary passageways 148 and 148' operate with opposing ends of line 100. It is also noted that in alternative embodiments primary passageway(s) and/or the secondary passageways need not be elongated to allow the line passing therethrough to slide toward opposing sides 19 and 21 of body 12 as previously discussed with regard to line lock 10.

Figure 11:
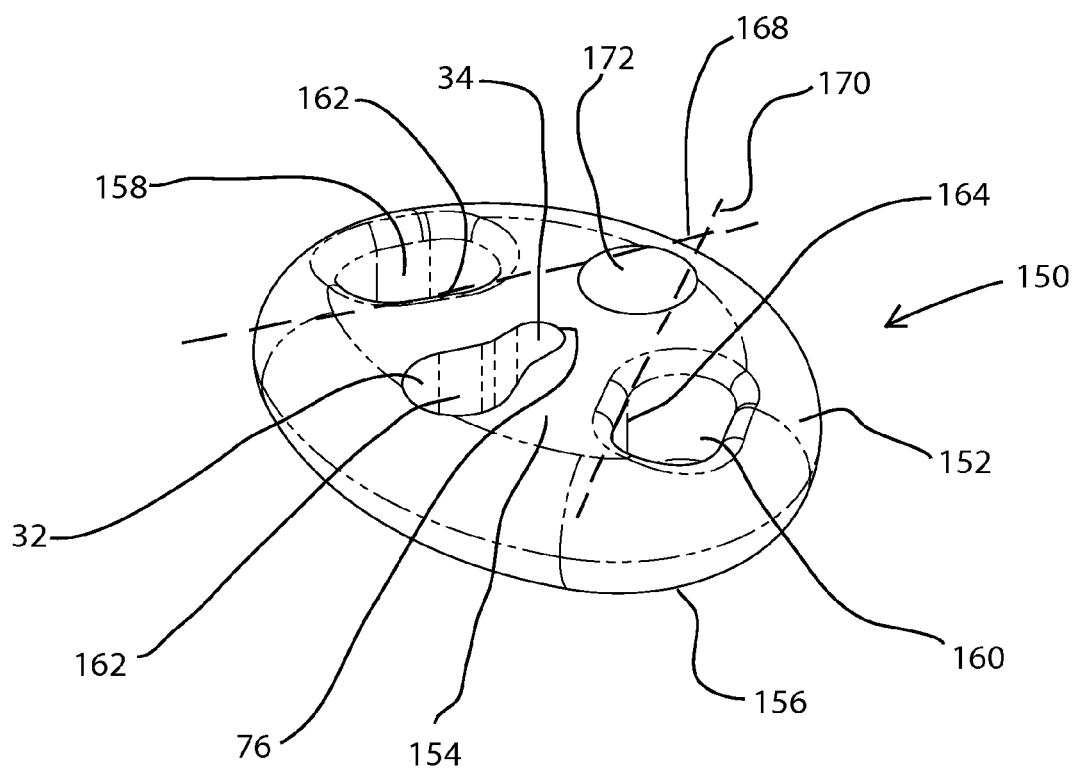
FIG. 11 is a perspective view of a line lock for use with a single strand of line.

Depicted in FIG. 11 is an alternative embodiment of a line lock 150 that is designed to slide along a single strand of line 100. Line lock 150 comprises a substantially disk shaped body 152 having a top surface 154 and an opposing bottom surface 156. Extending through body 152 between surfaces 154 and 156 is a primary passageway 158 and a spaced apart secondary passageway 160. Disposed between passageways 158 and 160 is a working passageway 162. Similar to line lock 10, working passageway 162 of line lock 150 has a first end with enlarged access region 32 and an opposing second end with constricted capture slot 34 thereat.

Primary passageway 158 and secondary passageway 160 have substantially the same elongated circular configuration which is similar to previously discussed secondary passageway 24. Each of passageways 158 and 160 has an inside face 162 and 164, respectively, that is disposed toward working passageway 162. Each inside face 162 and 164 is substantially disposed in or is tangent to a corresponding plane 168 and 170, respectively. Planes 168 and 170 converge toward capture slot 34 of working passageway 162 and diverge away from access region 32.

Also extending through body 152 between top surface 154 and bottom surface 156 is an end passageway 172. Although end passageway 172 can be positioned at a variety of different locations, end passageway 172 is shown aligned with working passageway 162 such that a plane extending between working passageway 162 and end passageway 172 separates primary passageway 158 from secondary passageway 160.

Figure 12A:
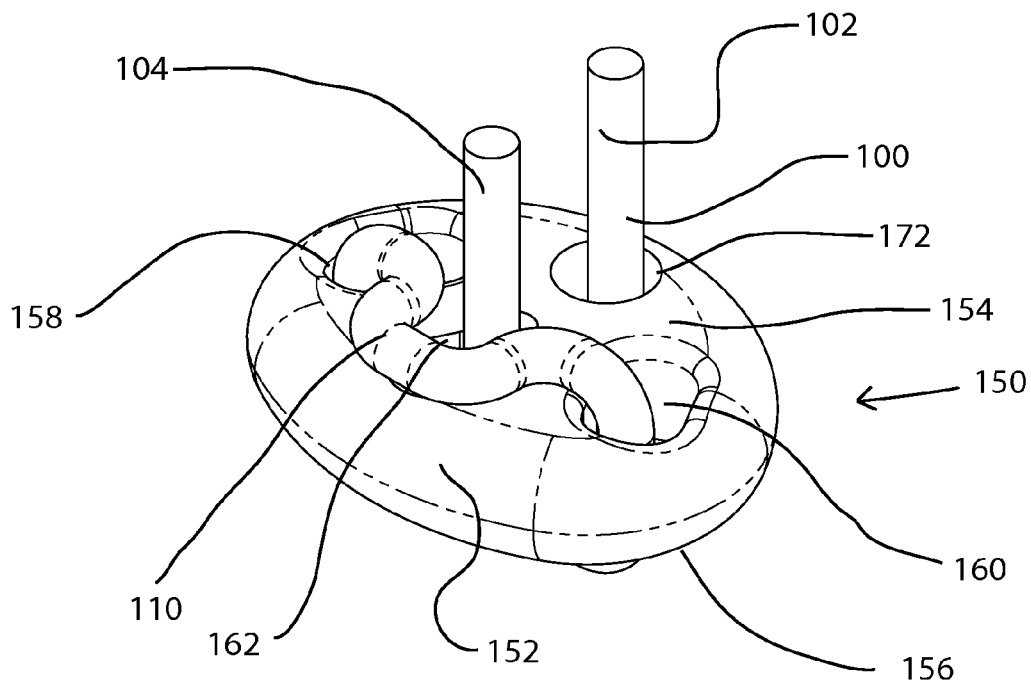
FIG. 12A is a perspective view of the line lock shown in FIG. 11 with a line routed therethrough.
Figure 12B:
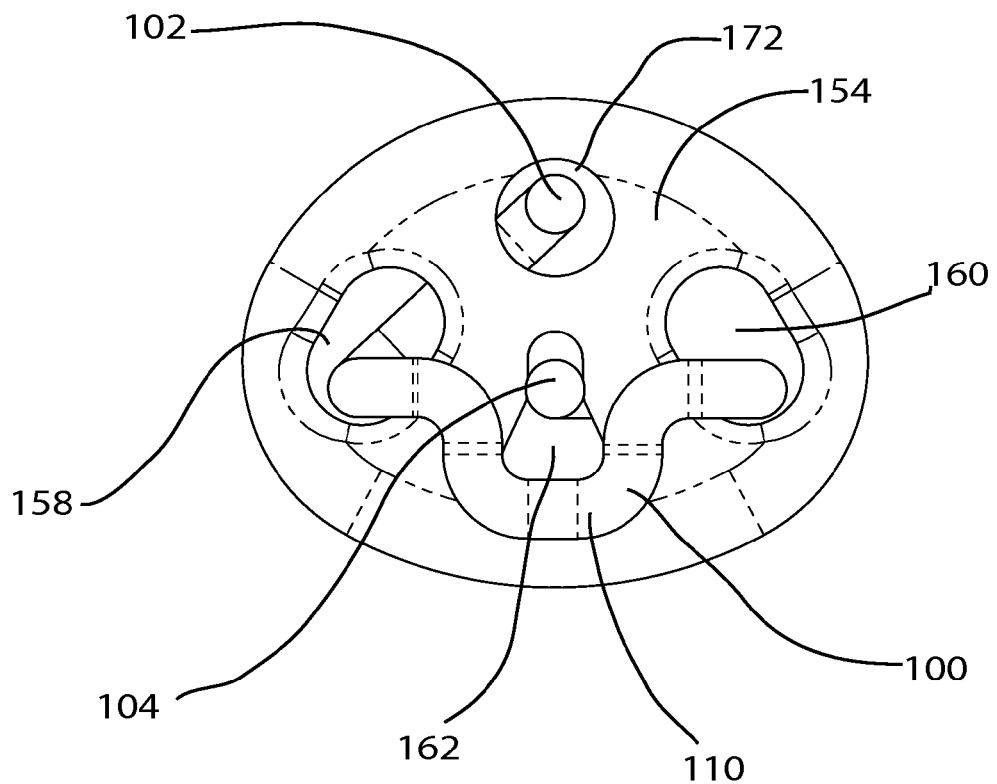
FIG. 12B is a top plan view of the line lock shown in FIG. 12A.
Figure 12C:
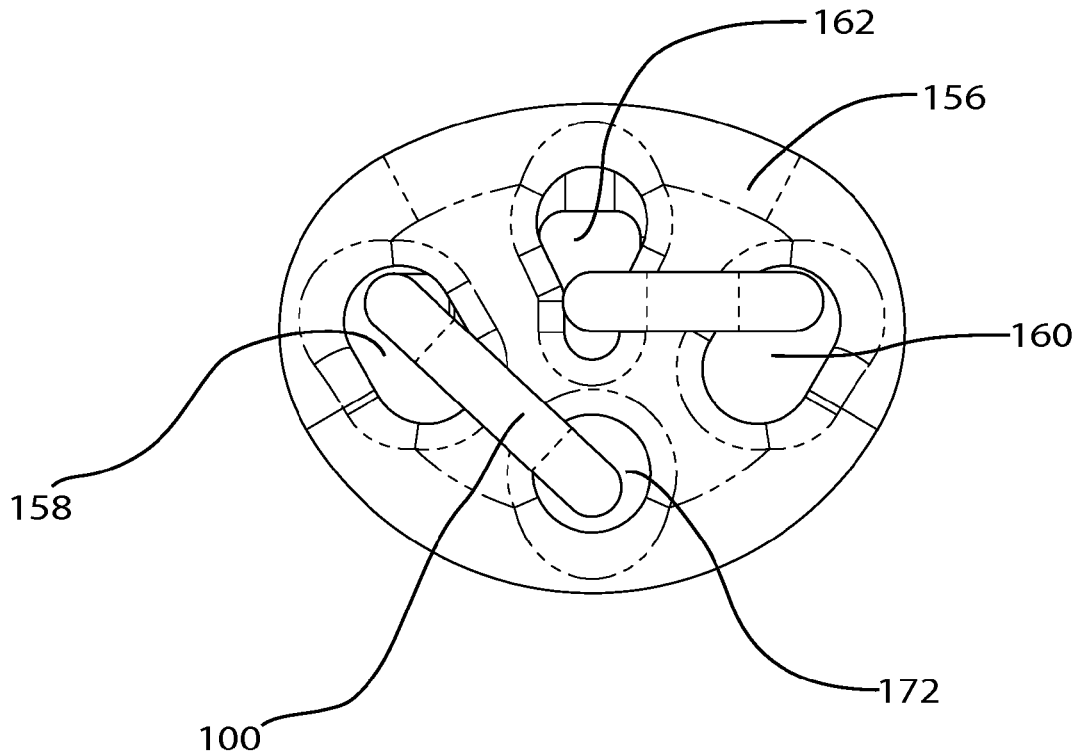
FIG. 12C is a bottom plan view of the line lock shown in FIG. 12A.

During use, as depicted in FIGS. 12A-12C, line 100 is routed through line lock 150 by passing working portion 104 from top surface 154 to bottom surface 156 through end passageway 172, up through primary passageway 158, down through secondary passageway 160, and finally up through working passageway 162. Compression portion 110 of line 100 extends between primary passageway 158 and secondary passageway 160 and is positioned to act upon working portion 104. Line lock 150 can be selectively advanced by pulling working portion 104 away from top surface 154 so that line 100 travels through line lock 150. Alternatively, line lock 150 can be manually slid toward standing portion 102. In either event, the length of standing portion 102 is decreased.

As line 100 is tensioned on line lock 150, line 100 locks on line lock 150 in substantially the same manner that line 100 locks with working passageway 28 as previously discussed with regard to line lock 10. That is, compression portion 110 forces working end 104 toward capture slot 34 so that the portion of line 100 within working passageway 162 is captured by wedged frictional engagement within capture slot 34. Furthermore, compression portion 110 either directly or indirectly biases working portion 104 against the top outside corner 76 of working passageway 162 at the second end thereof so as to increase the frictional engagement between line 100 and line lock 150. Line lock 150 thus provides a continuously adjustable line lock or a one way sliding stop. In alternative embodiments, it is appreciated that line lock 150 can be modified in at least the same ways as discussed with the other line locks disclosed herein.

The embodiment shown in FIGS. 12A-12C is advantageous in certain applications where line lock 150 is positioned behind a first object and working portion 104 and standing portion 102 pass through the first object. In this situation, standing portion 102 is fixed to a second object. By pulling on working portion 104, the first object is drawn irreversibly toward the second object. This is an advantage with surgical sutures where standing end 102 of a suture is attached to normal tissues and line lock 150 is placed behind tissue that has torn away. Standing portion 102 and working portion 104 pass through the torn tissue toward the normal tissue. By pulling on working portion 104 of suture, the torn tissue is pulled into apposition with the normal tissues and line lock 150 maintains the torn tissue adjacent to the normal tissue to facilitate healing of the tissue.

Figure 13A:
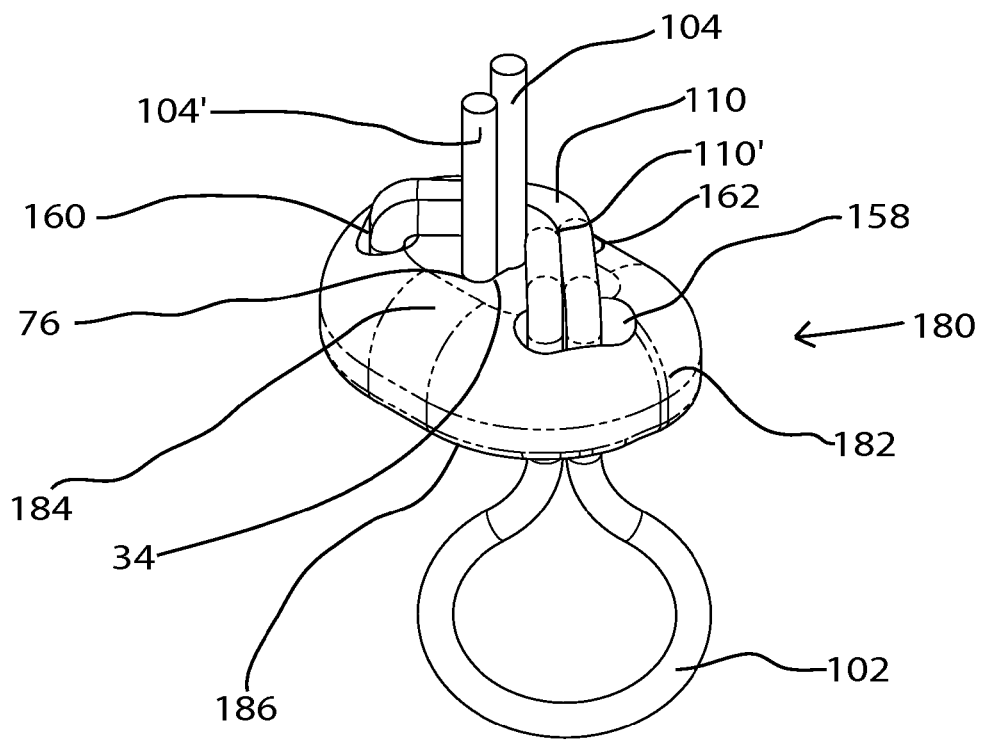
FIG. 13A is a top perspective view of a line lock having dual strands of line routed therethrough.
Figure 13B:
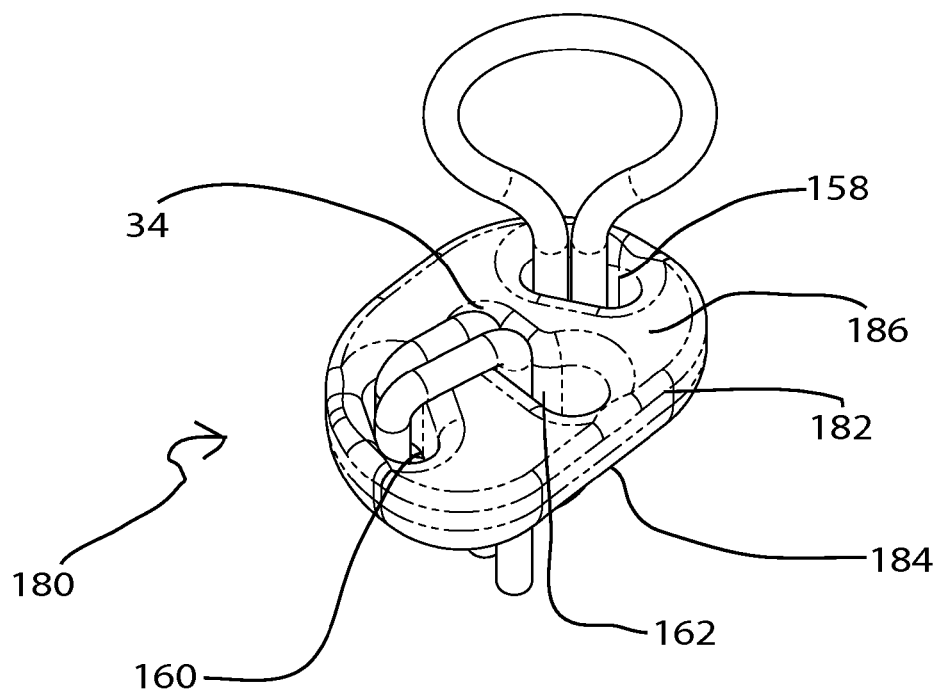
FIG. 13B is a bottom perspective view of the line lock shown in FIG. 13A.

Depicted in FIGS. 13A and 13B is another embodiment of a line lock 180 incorporating features of the present invention. Line lock 180 also comprises a substantially disk shaped body 182 having a top surface 184 and an opposing bottom surface 186. As with line lock 150, line lock 180 includes primary passageway 158, secondary passageway 160, and working passageway 162. Again, although not required, working passageway 162 is disposed such that a geometric line segment can be extended between primary passageway 158 and secondary passageway 160 so that the line segment intersects with working passageway 162. In contrast to line lock 150, line lock 180 does not include end passageway 172.

Each of passageways 158, 160, and 162 is configured to receive a double strand of line 100. Specifically, during use both working end 104 and 104' are passed up through primary passageway 158, down through secondary passageway 160 and then back up through working passageway 162. As a result, standing portion 102 is again formed in a loop that can be looped around, passed through, or otherwise secured to tissue or other structure. Unwanted slack is removed from standing portion 102 by again sliding line lock 180 on line 100 toward standing portion 102 and/or by pulling on one or both of working portions 104 and 104' so that line 100 passes through line lock 180.

When line 100 is tensioned on line lock 180, compression portions 110 and 110' force working portions 104, 104' toward capture slot 34 so that a portion of each line section passing through working passageway 162 is captured by wedged frictional engagement within capture slot 34. Compression portions 110 and 110' also bias working portions 104 and 104' toward and/or against top outsider corner 76 of working passageway 162 so as to increase the frictional engagement between line 100 and line lock 180. As previously discussed with passageways 22, 24, and 28 of line lock 10 in FIGS. 1-6, the radius of curvature of the top outside corner and bottom outside corner of each passageway 158, 160, and 162 can be set so as to further control the ability of line 100 to slide or not slide through the passageway. Other alternatives as discussed with the line locks herein are also applicable to line lock 180. In particular each of the passageways 158, 160, and 162 can also be configured to receive a single strand of line 100. In this configuration the single strand of line 100 is routed in a manner as described above for the double strand of line 100. Instead of the standing portion 102 forming a loop when a double strand of line 100 is used, in this case the standing portion 102 consists of a free end which can be attached to tissue or other structures.

Figure 14A:
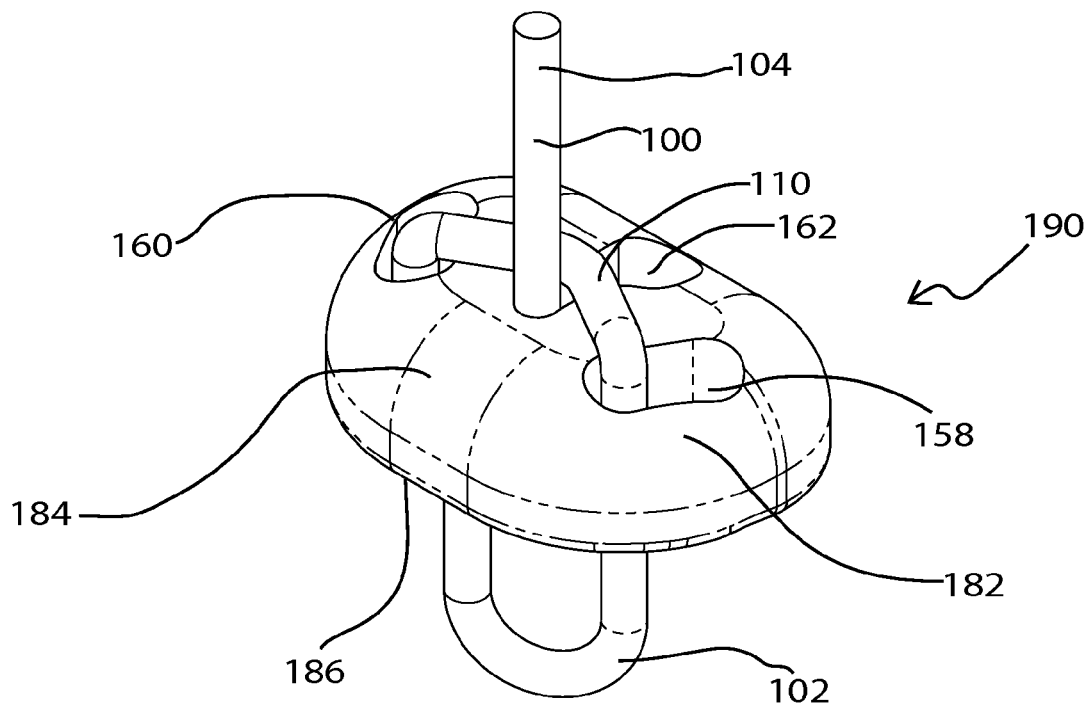
FIG. 14A is a top perspective view of a line lock having a line secured thereto.
Figure 14B:
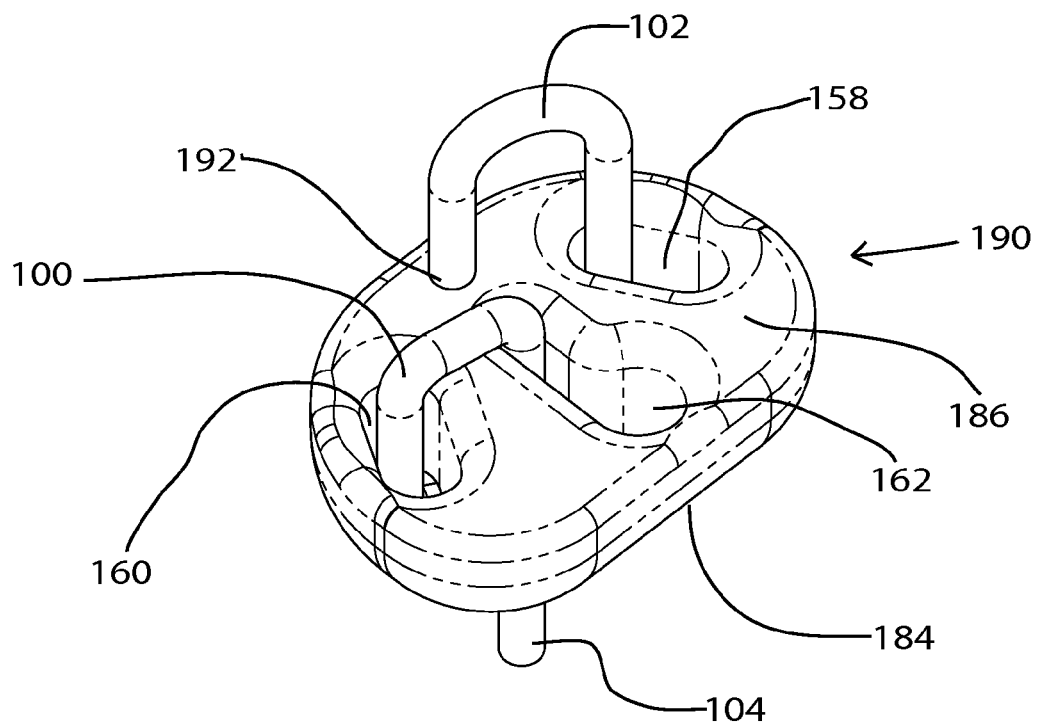
FIG. 14B is a bottom perspective view of the line lock shown in FIG. 14A.

Depicted in FIGS. 14A and 14B is still another embodiment of a line lock 190 incorporating features of the present invention. Line lock 190 has substantially the same configuration as line lock 180 with like elements being referenced with like reference characters. The primary distinction between line locks 180 and 190 is that in line lock 190, an end 192 of line 100 adjacent to standing portion 102 is secured to bottom surface 186 of body 182. End 192 can be secured to body 182 by being integrally molded into body 182 or can be otherwise secured such as by welding or mechanical attachment.

Line lock 190 is also distinguished from line lock 180 in that passageways 158, 160, and 162 need only be configured to receive a single strand of line 100. That is, working end 104 passes up through primary passageway 158, down through secondary passageway 160, and then back up through working passageway 162. Standing portion 102 is again substantially formed into a loop extending from end 192 of line 100 to primary passageway 158. Because end 192 of line 100 is secured to body 182, unwanted slack can be removed from standing portion 102 by pulling line 100 through line lock 190 and/or sliding line lock 190 down line 100. Line 100 is locked to line lock 190 in substantially the same manner as discussed above with regard to the other line locks when line 100 is tensioned on line lock 190.

Figure 15:
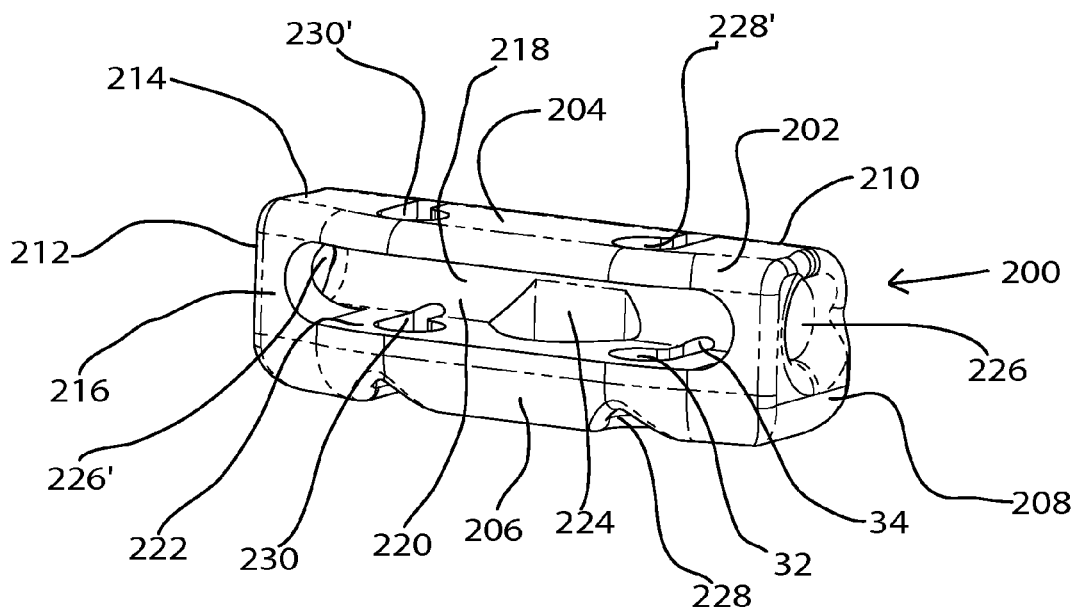
FIG. 15 is a perspective view of an alternative embodiment of a line lock.

Depicted in FIG. 15 is still another embodiment of a line lock 200 incorporating features of the present invention. Line lock 200 comprises an elongated substantially box shaped body 202 comprising a top wall 204 and an opposing bottom wall 206 each extending between a first side wall 208 and a first end 210 and an opposing second side wall 212 and an opposing second end 214. Also extending between top wall 204 and bottom wall 206 is a front wall 216 and an opposing back wall 218.

Partially bounded within body 202 is a hollow chamber 220. An access channel 222 is formed on front wall 216 so as to communicate with chamber 220. Also communicating with chamber 220 is a primary passageway 224. Primary passageway centrally extends through bottom wall 206 to chamber 220. A first secondary passageway 226 extends through first side wall 208 so as to communicate with chamber 220 while a second secondary passageway 226' extends through second side wall 212 so as to communicate with chamber 220. A pair of first working passageways 228 and 228' extend through bottom wall 206 and top wall 204, respectively, in vertical alignment between primary passageway 224 and first secondary passageway 226.

Similarly, a pair of second working passageways 230 and 230' extend through bottom wall 206 and top wall 204 in vertical alignment between primary passageway 224 and second secondary passageway 226'. As with the prior working passageways, each of working passageways 228, 228' and 230, 230' has a first end towards front wall 226 with an enlarged axis region 32 and an opposing second end toward back wall 218 with a capture slot 34 formed thereat.

Figure 16A:
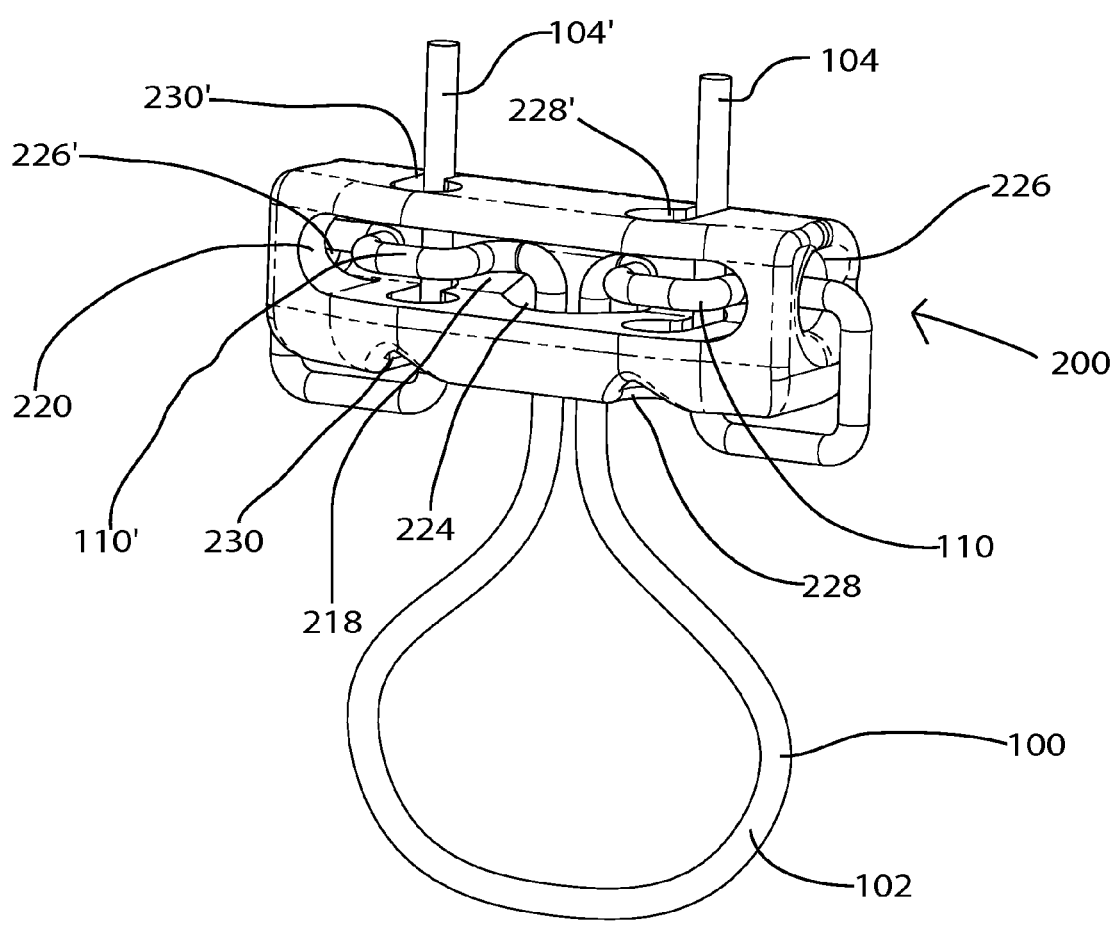
FIG. 16A is a perspective view of the line lock shown in FIG. 15 with a line routed therethrough.
Figure 16B:
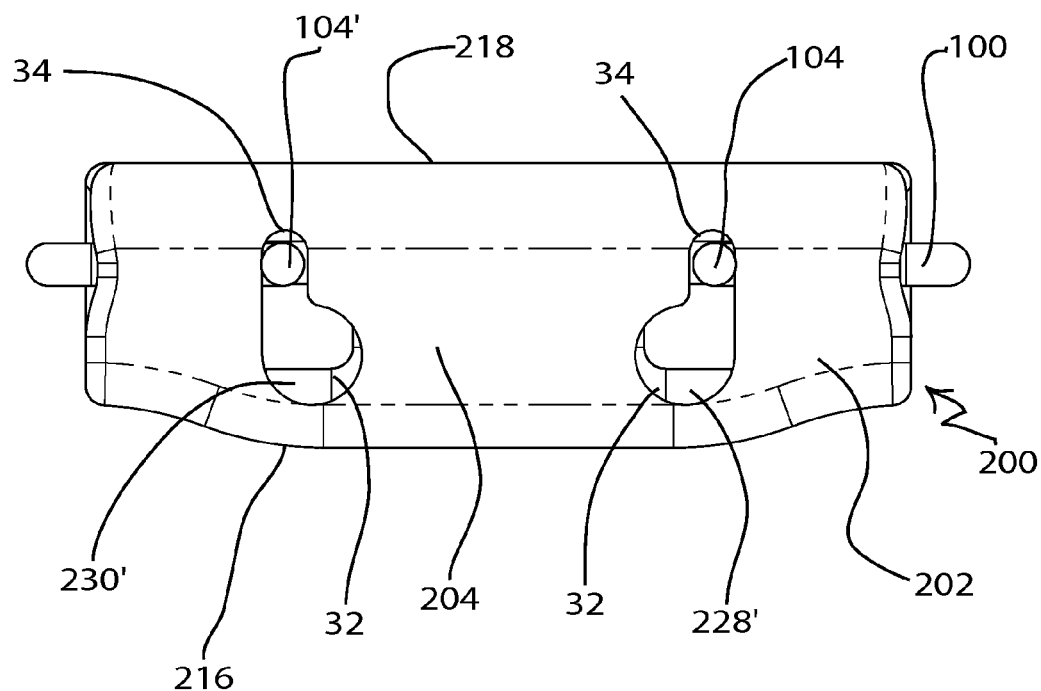
FIG. 16B is a top plan view of the line lock shown in FIG. 16A.
Figure 16C:
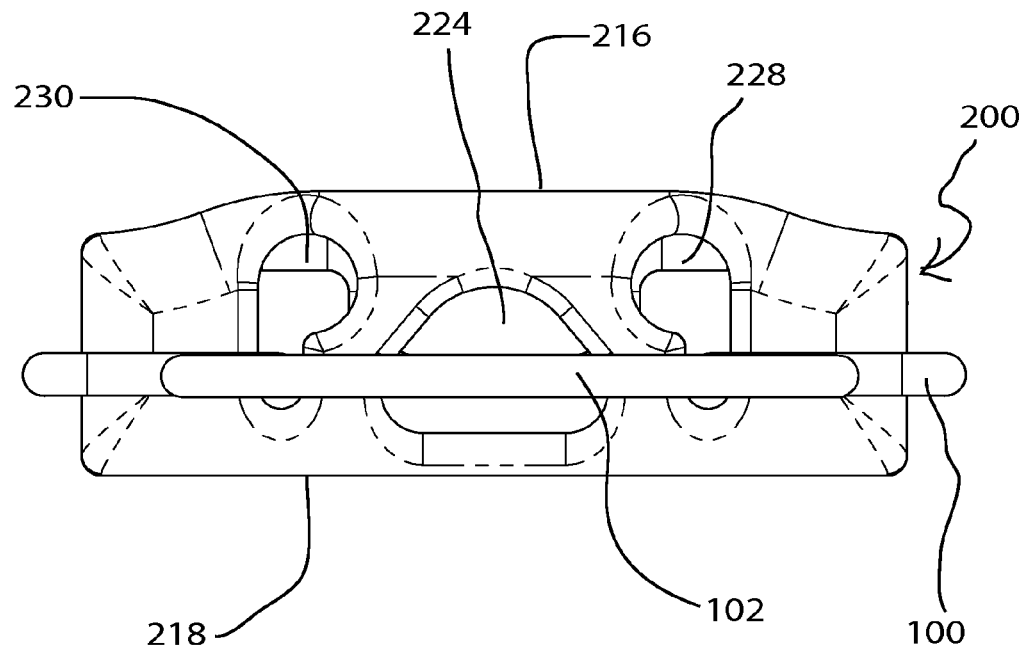
FIG. 16C is a bottom plan view of the line lock shown in FIG. 16A.

During use, as depicted in FIG. 16A-16C, working portions 104 of line 100 are passed up through primary passageway 224 into chamber 220. Working portion 104 then passes out of chamber 220 through first secondary passageway 226. Finally, working portion 104 passes up through first working passageway 228, through chamber 220, and then out through first working passageway 228'. Compression portion 110 of line 100 extends from primary passageway 224 to first secondary passageway 226. Working portion 104 is routed such that line 100 passes between compression portion 110 and back wall 218.

In like manner, working portion 104' extends from chamber 220 out through second secondary passageway 226'. Working portion 104' then extends up through second working passageway 230, through chamber 220, and then out through second working passageway 230'. Again, line 100 extends between compression portion 110' and back wall 218.

As with the other embodiments, line lock 200 can be slid along line 100 and/or line 100 can be pulled therethrough so as to remove all unwanted slack from standing portion 102. As line 100 is tension on line lock 200, compression portions 110 and 110' force the portion of line 100 extending between first working passageways 228 and 228' and between second working passageways 230 and 230', respectively, toward corresponding capture slots 34. As a result, at least a portion of line 100 extending through each of the working passageways is captured by frictional wedge engagement within each of the corresponding capture slots 34. Line 100 is thus locked with line lock 200.

Line lock 200 offers several advantages. When standing end 102 is slack and working ends 104 and 104' are tensioned, the sections of line 100 extending between working passageways 228 and 228' and between working passageways 230 and 230' force compression portions 110 and 110', respectively, back toward front wall 216 so as to allow the free travel of line 100 through line lock 200. In contrast, as discussed above, when tension is created in standing end 102 and slack is created in working ends 104 and 104', compression portions 110 and 110' force the sections of line 100 extending between working passageways 228 and 228' and between working passageways 230 and 230' toward back wall 218 so as to secure line 100 within the capture slots 34. This back and forth movement of compression portions 110 and 110' creates "backlash," or a finite distance that line lock 200 can move away from standing end 102 until locking of line 100 is achieved.

Top wall 204 of line lock 200 provides a physical constraint to the amount of movement seen in compression portions 110 and 110', thereby minimizing the amount of backlash. Furthermore, top wall 204 provides an additional friction point when compression portions 110 and 110' compress against line 100, thereby increasing the strength of the locking of line 100. That is, one friction point is located at working passageways 228 and 230 on bottom wall 206 and the second friction point is located at working passageways 228' and 230' on top wall 204.

It is again appreciated that the alternatives as discussed with the other embodiments are also applicable to line lock 200. By way of example and not by limitation, line 100 can be routed through line lock 200 in a manner analogous to the routing in FIG. 7. The various passageways can be open or closed as depicted in FIGS. 8 and 9. Similarly, line lock 200 can be divided in half and modified to function similar to the line locks shown in FIGS. 11-14.

Figure 17:
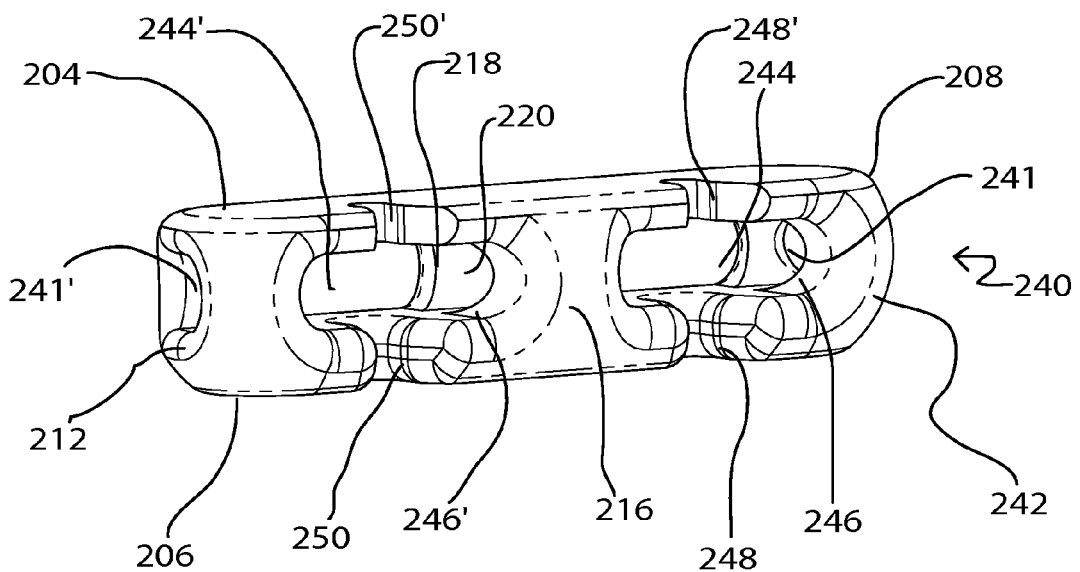
FIG. 17 is a perspective view of another alternative embodiment of a line lock.

Depicted in FIG. 17 is a final alternative embodiment of a line lock 240 incorporating features of the present invention. Line lock 240 has a configuration similar to line lock 200 and thus like elements are identified by like reference characters. Line lock 240 comprises an elongated substantially box shaped body 242. Similar to line lock 200, body 242 comprises top wall 204 and bottom wall 206 extending between side wall 208 and side wall 212. Body 242 also includes front wall 216 and back wall 218 which partially bound chamber 220.

In contrast to line lock 200, a first primary passageway 241 extends through first side wall 208 while second primary passageway 241' extends through second side wall 212. Primary passageways 241 and 241' each communicate with chamber 220. Body 242 of line lock 240 further comprises a first secondary passageway 244 extending through back wall 218 in communication with chamber 220 and a spaced apart second secondary passageway 244' in communication with chamber 220. A first access port 246 extends through front wall 216 in alignment with first secondary passageway 244' so as to communicate with chamber 220. Similarly, a second access port 246' extends through front wall 216 in alignment with second secondary passageway 244 so as to also communicate with chamber 220.

Furthermore, in contrast to the bounded working passageways of line lock 200, line lock 240 comprises a pair of first working passageways 248 and 248'. Working passageway 248 comprises a constricting slot that is formed on bottom wall 206 and is open along intersecting front wall 216. First working passageway 248' is aligned with first working passageway 248 and is formed on top wall 204 so as to also be open along intersecting front wall 216. A pair of second working passageways 250 and 250' are similarly formed on bottom wall 206 and top wall 204 so as to be aligned with second secondary passageway 244'. Each of the working passageways terminates at capture slot having a width substantially equal to or smaller than the diameter of line 100.

Figure 18A:
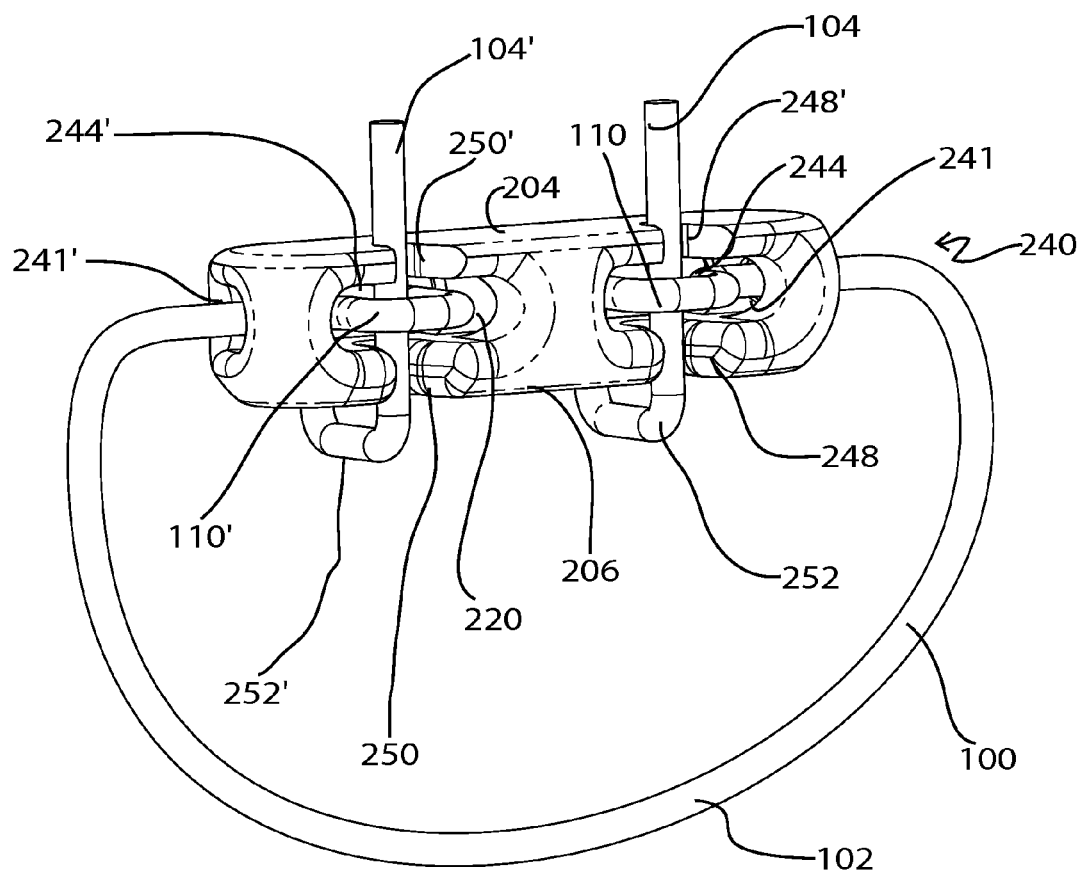
FIG. 18A is a perspective view of the line lock shown in FIG. 17 with a line routed therethrough.
Figure 18B:
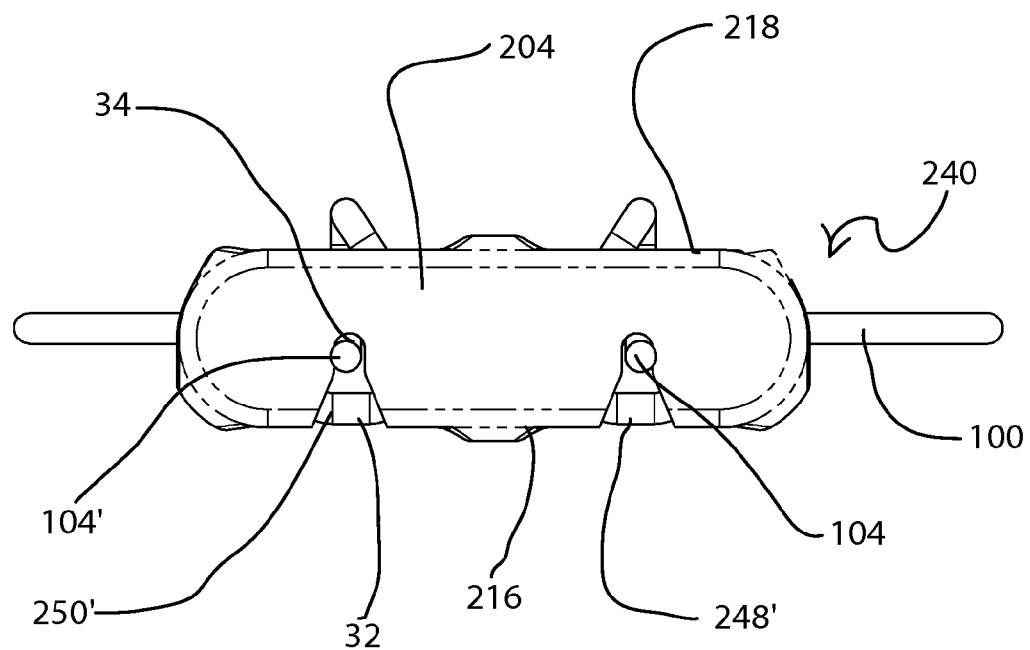
FIG. 18B is a top plan view of the line lock shown in FIG. 18A.
Figure 18C:
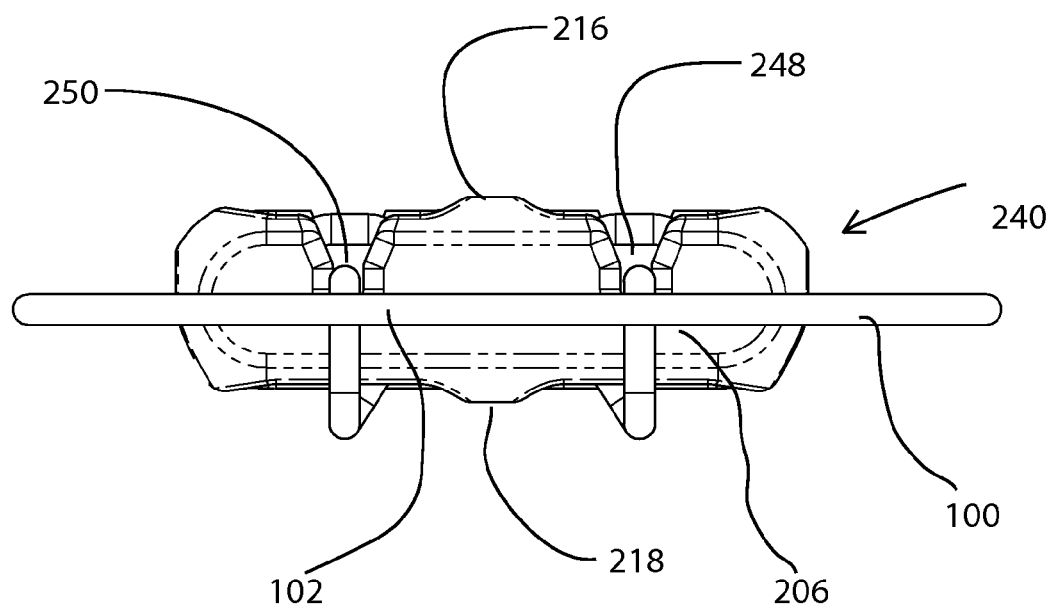
FIG. 18C is a bottom plan view of the line lock shown in FIG. 18A.

During use, as depicted in FIGS. 18A-18C, working end 104 of line 100 is passed through first primary passageway 242 into chamber 220 and then out through first secondary passageway 244. Working end 104 then passes down around bottom wall 206 and is then fed up through first working passageways 248 and 248'. A compression portion 110 of line 100 extends between primary passageway 241 and secondary passageway 244. Working portion 104 is passed between working passageways 248, 248' so that line 100 passes between compression portion 110 and first secondary passageway 244.

Working portion 104' is similarly passed through the passageways on the opposing side of line lock 240. That is, working portion 104' passes through primary passageway 241' and into chamber 220. Working portion 104' then travels out through secondary passageway 244', bends around bottom wall 206, and then travels up through working passageways 250 and 250'.

In the above configuration, slack can be removed from standing portion 102 by pulling line 100 through line lock 240 and/or sliding line lock 240 toward standing portion 102. As line 100 tensions on line lock 240, compression portions 110 and 110' again force portions of line 100 into capture slots 34 of the working passageways so as to secure line 100 to line lock 240 by wedged frictional engagement.

Like line lock 200, line lock 240 provides containment of compression portions 110 and 110' to minimize backlash.

Unlike the other embodiments, line 100 is routed through line lock 240 such that at least one line turn exceeds 90 degrees. For example, the transition between compression portions 110 and 110' and looping portions, designated as 252 and 252', respectively, create 180 degree turns in line 100. These sharp bends in line 100 increase the friction that must be overcome in order to advance line lock 240 toward standing end 102. However, the sharp bends also contribute to greater locking strength of line lock 240 to line 100. This embodiment is beneficial when line 100 is monofilament or single strand line, due to the commonly lower line on line friction and greater flexural stiffness of monofilament line when compared to braided or twisted strand line.

Figure 19:
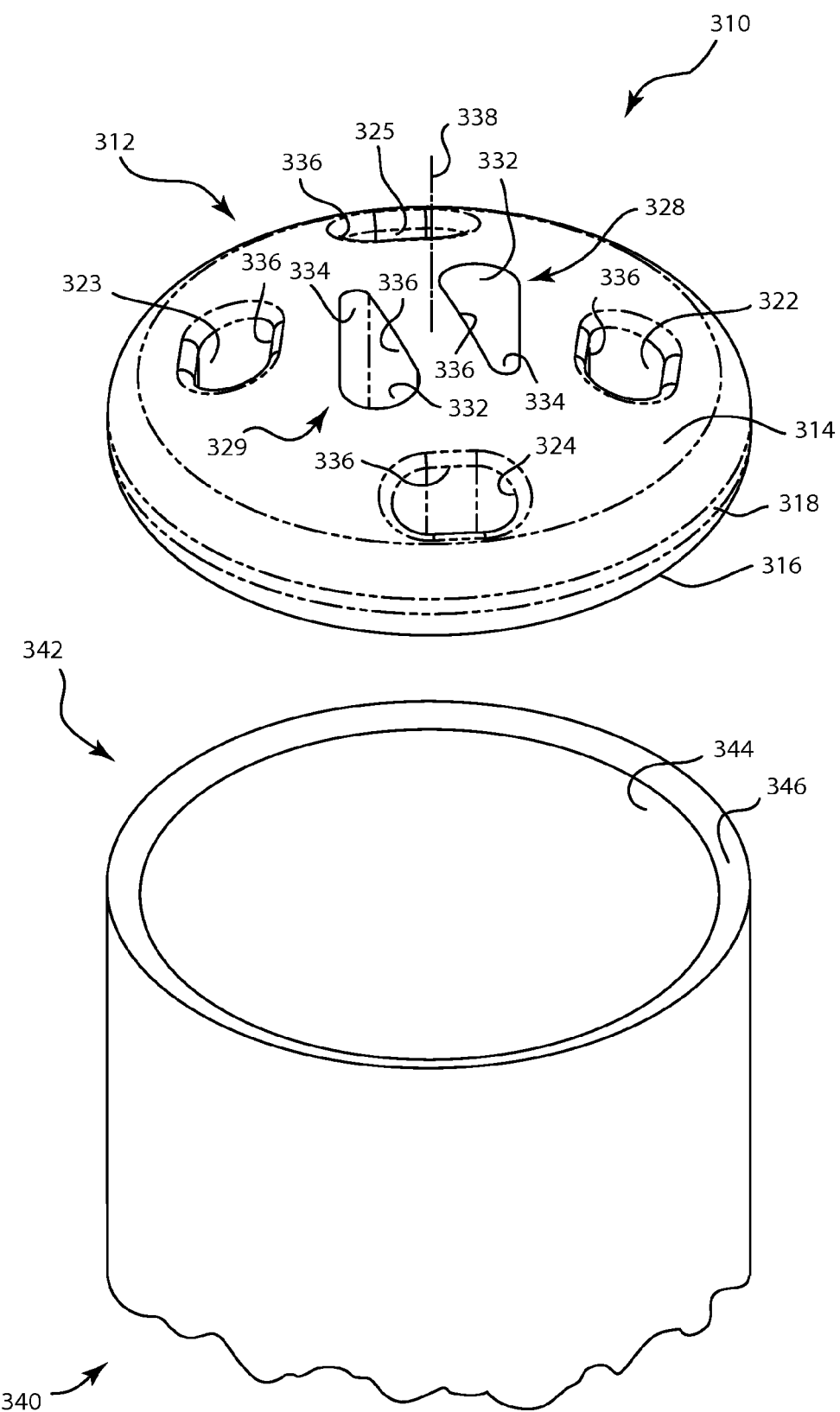
FIG. 19 is a perspective view of a line lock according to another alternative embodiment of the invention, with an associated insertion tool.

Referring to FIG. 19, a perspective view illustrates a line lock 310 according to one alternative embodiment of the invention. As shown, the line lock 310 has a body 312 that is generally disc-shaped. The body 312 has a top surface 314, a bottom surface 316, and a periphery 318 that extends between the top surface 314 and the bottom surface 316 to define a generally circular profile. In this application, a shape having a "generally circular profile" is any shape in which the outside boundary of any cross section passing through the main portion of the shape is substantially circular.

The body 312 bounds a plurality of passageways designed to cooperate receive a line such as a suture. In this application, passageways that "cooperate to receive" a line such as a suture receive the line such that the line passes through all of the cooperating passageways. The passageways of the body 312 include a first primary passageway 322 and a second primary passageway 323, each of which may be positioned adjacent to the periphery 318. The primary passageways 322, 323 are positioned on opposite sides of the body 312.

Furthermore, in the line lock 310 of FIG. 19, the passageways include a first secondary passageway 324 and a second secondary passageway 325, which are also positioned on opposite sides of the body 312, adjacent to the periphery 318. The secondary passageways 324, 325 may be positioned slightly closer to the periphery 318 than the primary passageways 322, 323. Yet further, the passageways also include a first working passageway 328 and a second working passageway 329. The working passageways 328, 329 are relatively centrally located with respect to the body 312.

Each of the primary and secondary passageways 322, 323, 324, 325 may be generally rounded, and may optionally be somewhat elongated to provide an oval cross-section capable of receiving a doubled-over suture end, as when a suture end (not shown) is inserted through a loop (not shown) and drawn through the primary and secondary passageways 322, 323, 324, 325 via the loop. Each of the working passageways 328, 329 may also have a cross-section broad enough to receive a doubled-over suture end.

The passageways 322, 323, 324, 325, 328, 329 intersect the top surface 314 to form corresponding openings, each of which is bounded by one of a plurality of top outside corners 336. The passageways 322, 323, 324, 324, 328, 329 also intersect the bottom surface 316 to form corresponding openings, each of which is bounded by one of a plurality of bottom outside corners (not shown).

As in the description previously set forth, some or all of the top outside corners 336 may have a smaller (i.e., sharper) radius than the corresponding bottom outside corners. More particularly, the top outside corners 336 of the working passageways 328, 329 may have comparatively small radii when compared to the bottom outside corners. In fact, in the embodiment of FIG. 19, the radii of the top outside corners 336 of the working passageways 328, 329 are considerably sharper than those of the top outside corners 336 of the primary and secondary passageways 322, 323, 324, 325. The sharp radii of the top outside corners 336 of the working passageways 328, 329 enhances locking of the suture by the line lock 310.

Each of the working passageways 328, 329 may have a shape that also facilitates locking of the suture, such as the teardrop-shaped cross-section illustrated in FIG. 19. More precisely, each of the working passageways 328 may have an access region 332 and a capture slot 334. The access region 332 is large enough to permit the suture to pass therethrough with clearance. However, the capture slot 334 may be somewhat narrower such that, when the suture is drawn into the capture slot 334, the walls of the capture slot 334 press against the suture to restrict further motion of the suture through the slot 334. The operation of the capture slot 334 will be further shown and described in connection with FIGS. 20 and 21.

In the embodiment of FIG. 19, the first primary, secondary, and working passageways 322, 324, 328 are symmetrically arranged about the center of the body 312 with respect to the second primary, secondary, and working passageways 323, 325, 329. In other words, the first primary, secondary, and working passageways 322, 324, 328 possess radial symmetry with respect to the second primary, secondary, and working passageways 323, 325, 329. Accordingly, if the first primary, secondary, and working passageways 322, 324, 328 were rotated 180° about a central axis 338 of the body 312, they would be substantially superimposed on the second primary, secondary, and working passageways 323, 325, 329.

According to one alternative embodiment, the capture slots 334 may extend at angles with respect to the access regions 332 so that the working passageways 328, 329 may be more compactly arranged, while keeping the capture slots 334 at the desired position and orientation with respect to the first primary and secondary passageways 322, 324 and with respect to the second primary and secondary passageways 323, 325. Such a configuration may potentially provide a more compact line lock (not shown) without losing suture locking capability.

In addition to the line lock 310, FIG. 19 also illustrates an insertion tool 340 that may be used to insert a line lock such as the line lock 310 of FIG. 19 into a relatively constricted space, such as a space within the body accessed via a cannula or the like. The insertion tool 340 has a proximal end (not shown), which may have handle or other structure to facilitate grasping by hand. The insertion tool 340 also has a distal end 342 and a hollow bore 344 that may extend along the entire displacement between the proximal end and the distal end 342 so that sutures or other items can be inserted into one end of the hollow bore 344 and retrieved from the opposite end. The distal end 342 has a rim 346, which may have an annular shape, a frustoconical shape, or the like, such that the body 312 is able to seat against the rim 346. The insertion tool 340 can thus be used to advance the line lock 310. The insertion tool 340 is illustrated proximate the bottom side 316 of the body 312 for clarity in FIG. 19; however, in use, the insertion tool 340 generally abuts the top side 314 and the periphery 318. The manner in which the insertion tool 340 is used to advance the line lock 310 will be more fully set forth in the description of FIG. 20.

Figure 20:
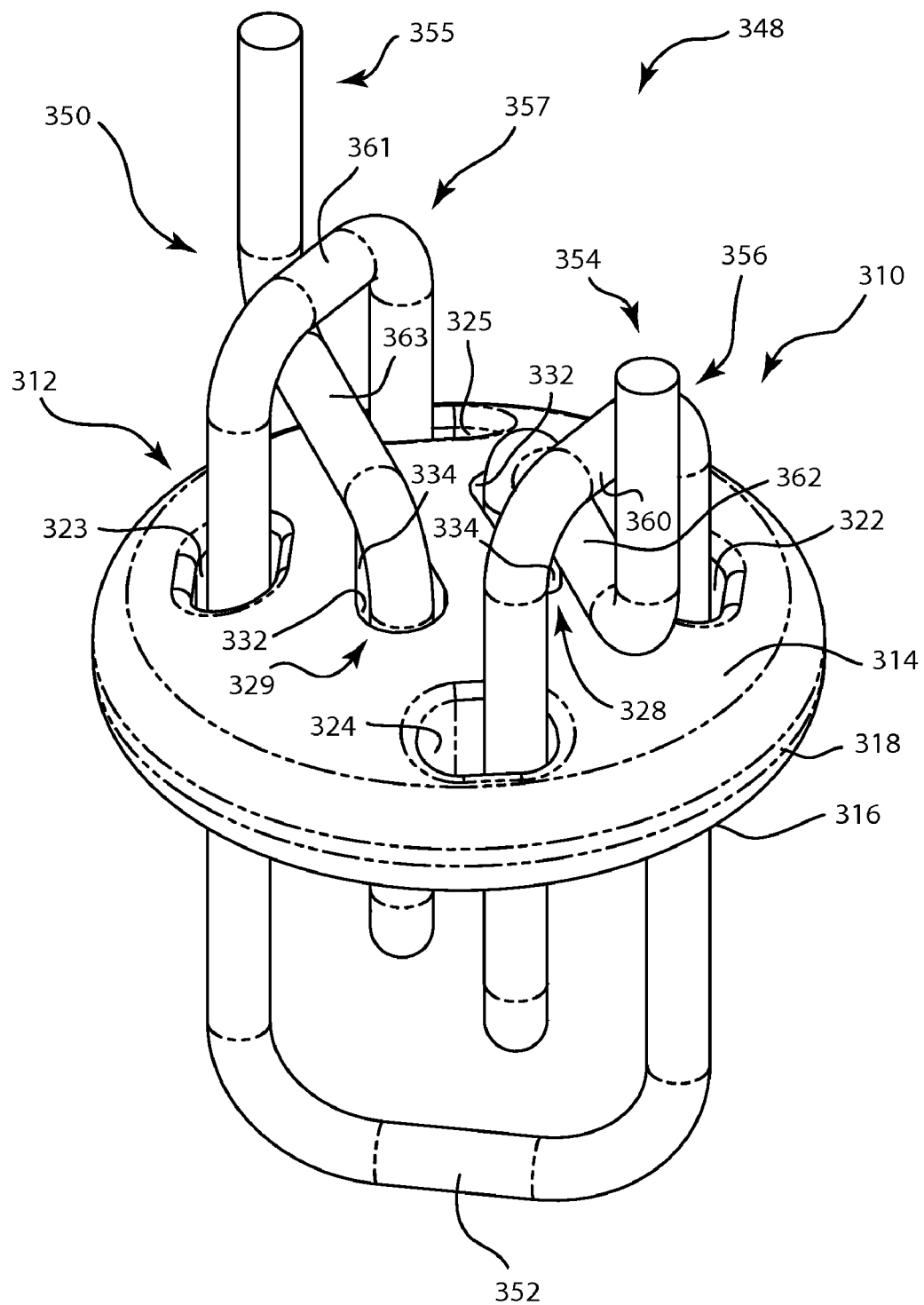
FIG. 20 is a perspective view of the line lock of FIG. 19, with a suture passing loosely through the passageways of the line lock.

Referring to FIG. 20, a perspective view illustrates a system 348 including the line lock 310 of FIG. 19 and a suture 350 relatively loosely passing through the passageways 322, 323, 324, 325, 328, 329 of the body 312. The suture 350 may be similar or identical to that described previously. Accordingly, the suture 350 may have a standing portion 352, which is the portion of the suture 350 that is placed under tension and constrained by advancement of the line lock 310, first and second working portions 354, 355, which are handled by a user, and first and second locking portions 356, 357 that are positioned between the standing portion 352 and the first and second working portions 354, 355, respectively.

The suture 350 may be inserted through the passageways 322, 323, 324, 325, 328, 329 according to a wide variety of methods. For example, the suture 350 may be inserted by hand. Alternatively, the suture 350 may be inserted through the use of threaders (not shown) that are initially routed through the passageways 322, 323, 324, 325, 328, 329 along the proper pathways. The threaders may have leading ends designed to be drawn by hand, and trailing ends with loops or other features capable of capturing and drawing the suture ends.

Thus, a user may simply attach the ends of the suture 350 to the trailing ends of the threaders, and then pull the threaders until the suture 350 passes through the passageways 322, 323, 324, 325, 328, 329 along the desired pathways. The ends of the suture 350 may then be removed from the trailing ends of the threaders. In addition to or in the alternative to the use of threaders, a cartridge (not shown) may be used to retain the line lock 310 and guide the suture 350 through the passageways 322, 323, 324, 325, 328, 329 along the desired pathways.

As illustrated in FIG. 20, the first locking portion 356 extends from the standing portion 352 through the first primary passageway 322, then through the first secondary passageway 324, and then through the first working passageway 328. From the first working passageway 328, the first working portion 354 extends between the top surface 314 and the section of the first locking portion 356 that passes from the first primary passageway 322 to the first secondary passageway 324. This section of the first locking portion 356 is a first compression section 360 of the suture 350.

Similarly, the second locking portion 357 extends from the standing portion 352 through the second primary passageway 323, then through the second secondary passageway 325, and then through the second working passageway 329. From the second working passageway 329, the second working portion 355 extends between the top surface 314 and the section of the second locking portion 357 that passes from the second primary passageway 323 to the second secondary passageway 325. This section of the second locking portion 357 is a second compression section 361 of the suture 350.

As shown in FIG. 20, the first and second working portions 354, 355 have first and second compressed sections 362, 363, respectively. The compressed sections 362, 363 underlie the corresponding compression sections 360, 361 of the first and second locking portions 356, 357, respectively. When the compression sections 360, 361 become taught, they press the compressed sections 362, 363 against the top surface 314 of the body 312. This will be explained in further detail subsequently.

The standing portion 352 may be inserted through and/or around some feature (not shown), such as bodily tissue, that is to be retained by the system 348. The standing portion 352 may additionally or alternatively pass through an opening of a bone anchor or the like to enable tissues to be anchored to the bone, as in rotator cuff repair. From the configuration of FIG. 20, the suture 350 may be tightened by advancing the line lock 310 along the standing portion 352. The line lock 310 may be advanced by holding the working portions 354, 355 and pressing the body 312 toward the standing portion 352.

According to one method, the line lock 310 may be advanced along the standing portion 352 through the use of a tool such as the insertion tool 340 of FIG. 19. More precisely, the working portions 354, 355 may first be inserted into the hollow bore 344 at the distal end 342. The working portions 354, 355 are inserted through the hollow bore 344 such that they protrude from the hollow bore 344 at the proximal end. A user may then grasp the working portions 354, 355 and draw them proximally, while holding the insertion tool stationary or advancing it distally, until there remains no slack in the working portions 354, 355, and the body 312 is seated against the rim 346 of the distal end 342. The shape of the rim 346 may tend to draw the body 312 into a position and orientation coaxial with the insertion tool 340 to facilitate insertion of the line lock 310 into a relatively narrow space.

Once the slack has been removed from the working portions 354, 355, further tension on the working portions 354, 355 tends to cause the locking portions 356, 357 to advance through the passageways 322, 323, 324, 325, 328, 329, moving from the primary passageways 322, 323 toward the working passageways 328, 329. Motion of the locking portions 356, 357 in this direction is relatively unrestricted since the compression sections 360, 361 remain slack, thereby allowing the locking portions 356, 357 to move through the access regions 332 of the working passageways 328, 329. Consequently, the line lock 310 is able to advance along the standing portion 352, thereby causing the standing portion 352 to tighten.

In alternative to use of a tool such as the insertion tool 340 of FIG. 19, the line lock 310 may be advanced along the standing portion 352 without any tooling. For example, the line lock 310 may be pressed and moved along the standing portion 352 by direct pressure from a finger. Alternatively, grasping the working portions 354, 355 and pulling them in substantially opposite and/or co-linear directions may cause the line lock 310 to advance along the standing portion 352. Each of the working portions 354, 355 may then lie along the top surface 314, but may not pass through the corresponding capture slot 334 until locking is performed. Such a technique may be particularly useful for retaining tissues in more readily accessible areas, where the working portions 354, 355 can be oriented and drawn in opposite directions. Use of insertion tooling may be more appropriate for more confined spaces.

Figure 21:
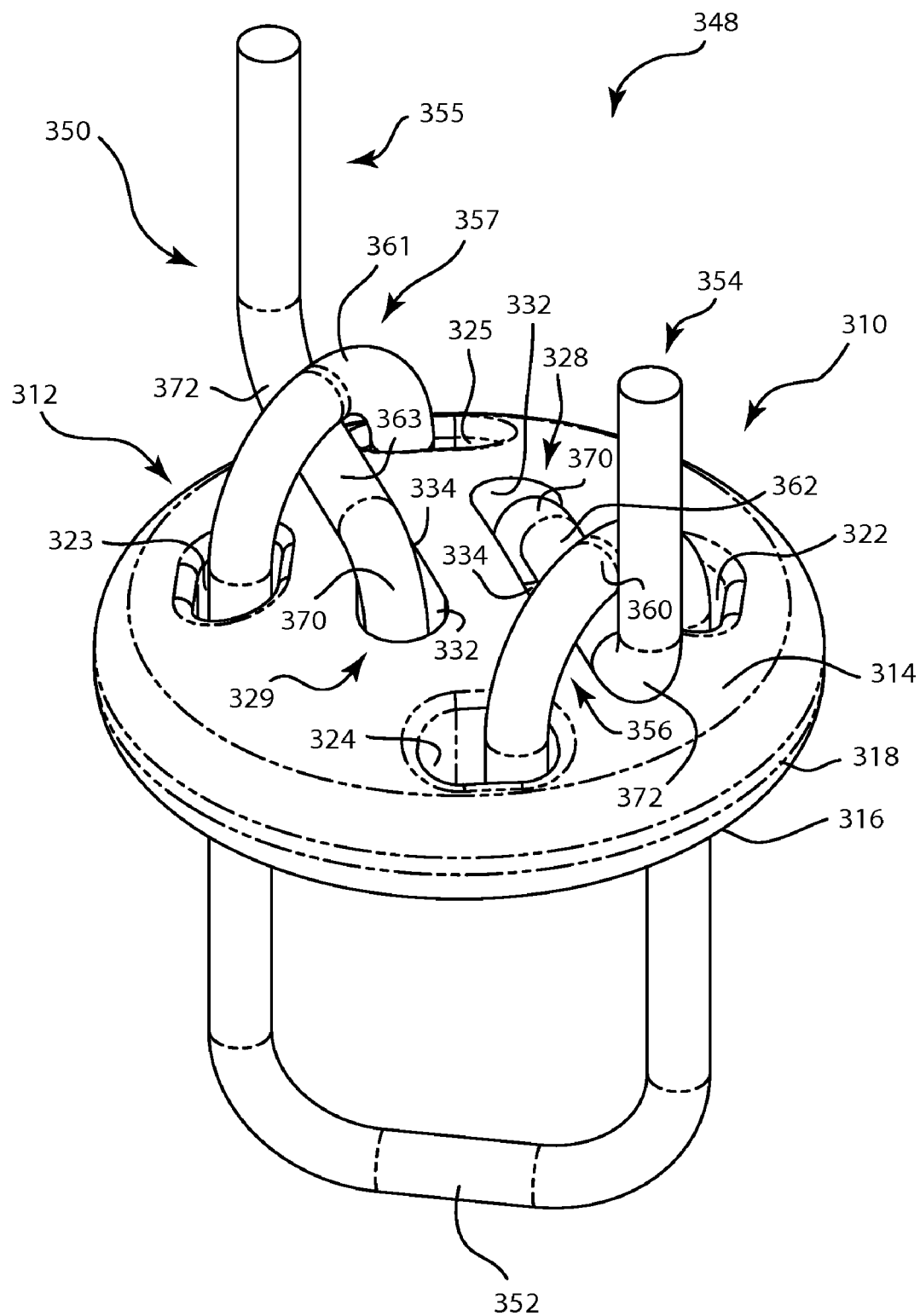
FIG. 21 is a perspective view of the line lock of FIG. 19, with the suture passing tightly through the passageways of the line lock.

Referring to FIG. 21, a perspective view illustrates the system 348 of FIG. 20, with the suture 350 routed relatively tightly through the passageways 322, 323, 324, 325, 328, 329. As the standing portion 352 tightens, tension in the standing portion 352 causes the compression sections 360, 361 to become taught. The compression sections 360, 361 straighten, thereby drawing the portions of the suture 350 within the working passageways 328, 329 outward, into the capture slots 334. The compressed sections 362, 363 of the working portions 354, 355 adjacent to the working passageways 328, 329 are pinned against the top surface 314 by the compression sections 360, 361.

Accordingly, each of the working portions 354, 355 is bent twice, with each bend having an angle of about ninety degrees. A first bend 370 is about the top outside corner 336 (as labeled in FIG. 19) of each corresponding working passageway 328, 329, and a second bend 372 is about the corresponding compression section 360, 361. As mentioned previously, the top outside corners 336 of the working passageways 328, 329 have tight radii. Accordingly, the top outside corners 336 of the working passageways 328, 329 provide relatively high friction surfaces, particularly when the working portions 354, 355 are pressed against them via tension, like that applied by the compression sections 360, 361. The compression sections 360, 361 may also provide considerable friction directly against the compressed sections 362, 363, depending on the structure and material of the suture 350.

Due to the friction applied to the bends 370, 372 of each of the working portions 354, 355 by the tensioned standing portion 352, the working portions 354, 355 are generally unable to retract back into the working passageways 328, 329. However, the standing portion 352 may still be tightened by further drawing on the working portions 354, 355. Tension in the working portions 354, 355 tends to pull the compression sections 360, 361 inward, thereby removing the bends 370, 372 and relieving the associated sources of friction. Further advancement of the body 312 along the standing portion 352 only increases the level of tension in the standing portion 352 so that, when tension on the working portions 328, 329 is relieved, the working portions 328, 329 are again drawn to the locked configuration.

After the locking portions 356, 357 have been locked via tension in the standing portion 352, the working portions 354, 355 may be cut short, for example, just outside the second bends 372. The friction on the bends 370, 372 keeps slippage to a level low enough that cutting the working portions 354, 355 in such a manner does not impair the operation of the line lock 310. The second bends 372 may disappear because there is no longer tension drawing the working portions 354, 355 to the orientation illustrated in FIG. 21. However, the second bends 372 are not required for locking; rather, the compression sections 360, 361 continue to press the compressed sections 362, 363 against the top surface 314, adjacent to the first bends 370. The friction of this compression interface, in addition to that of the first bends 370, is sufficient to keep the suture 350 from slipping back through the passageways 322, 323, 324, 325, 328, 329.

If desired, the line lock 310 and/or the suture 350 may be formed of bioabsorbable materials. Alternatively, the line lock 310 and the suture 350 may be small and compact enough that they can remain in the body indefinitely without causing any discomfort or significant health risks.

Figure 22:
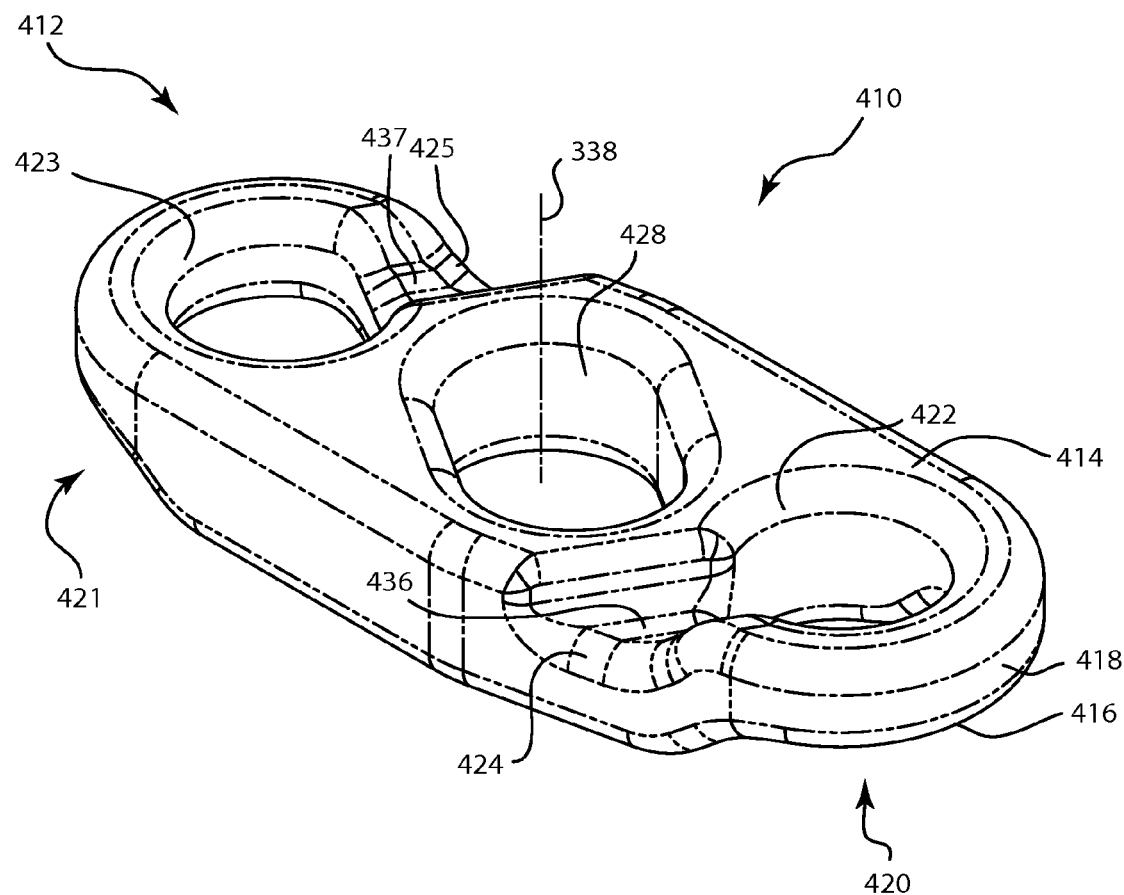
FIG. 22 is a perspective view of a line lock according to another alternative embodiment of the invention.

Referring to FIG. 22, a perspective view illustrates a line lock 410 according to another alternative embodiment of the invention. The line lock 410 has a body 412 that is generally elongated, and is compactly designed for less intrusive insertion into the body, and for more rapid bioabsorption. The body 412 has a top surface 414, a bottom surface 416, and a periphery 418 extending between the top surface 414 and the bottom surface 416 to provide the elongated profile of the body 412.

Furthermore, the body 412 is shaped to define a first primary passageway 422, a second primary passageway 423, a first secondary passageway 424, a second secondary passageway 425, and a first working passageway 428. The first and second primary passageways 422, 423 and the first working passageway 428 are all fully bounded. The first and second secondary passageways 424, 425 are each only partially bounded.

As mentioned previously, the term "passageway," as used in this application, is broadly interpreted to include partially bounded apertures, open channels, recesses, grooves, slots, and the like, that are capable of receiving a line and at least partially retaining the line therein. Accordingly, the structures labeled by reference numbers 424, 425 of FIG. 22 are, indeed, passageways. The secondary passageways 424, 425 are contiguous with the periphery 418 because the bore of each of the secondary passageways 424, 425 transitions directly into the periphery 418, with no significant intervening surface.

The first and second primary passageways 422, 423 are each generally circular in shape. The first working passageway 428 is designed to accommodate both locking portions 356, 357 of the suture 350 (not shown in FIG. 22), and is thus elongated in shape. The first working passageway is positioned between the first and second primary passageways 422, 423 such that the passageways 422, 423, 428 are arrayed in a generally straight line along the length of the body 412.

In FIG. 22, the first working passageway 428 has a generally rectangular shape, with semicircular arcs at the short ends. In alternative embodiments, any of a wide variety of shapes may be used, including trapezoidal, rectangular, square, triangular, circular, and oval shapes. If desired, alternative shapes may include one or more access regions and one or more capture slots, like those of the previous embodiment, that enhance suture locking.

The body 412 also defines a first groove 436 and a second groove 437, both of which are formed in the top surface 414. The first groove 436 extends along a generally straight path between the first primary and secondary passageways 422, 424. Similarly, the second groove 437 extends along a generally straight path between the second primary and secondary passageways 423, 425. The first and second grooves 436, 437 serve to enhance suture locking by the line lock 410 in a manner that will be set forth subsequently.

As shown in FIG. 22, the passageways 422, 423, 424, 425, 428 are symmetrical to each other about a central axis 338 of the body 412. This is because, if rotated 180° about the central axis 338, the first primary and secondary passageways 422, 424 would be superimposed on the second primary and secondary passageways 423, 425, and the first working passageway 428 would be superimposed on itself.

Figure 23:
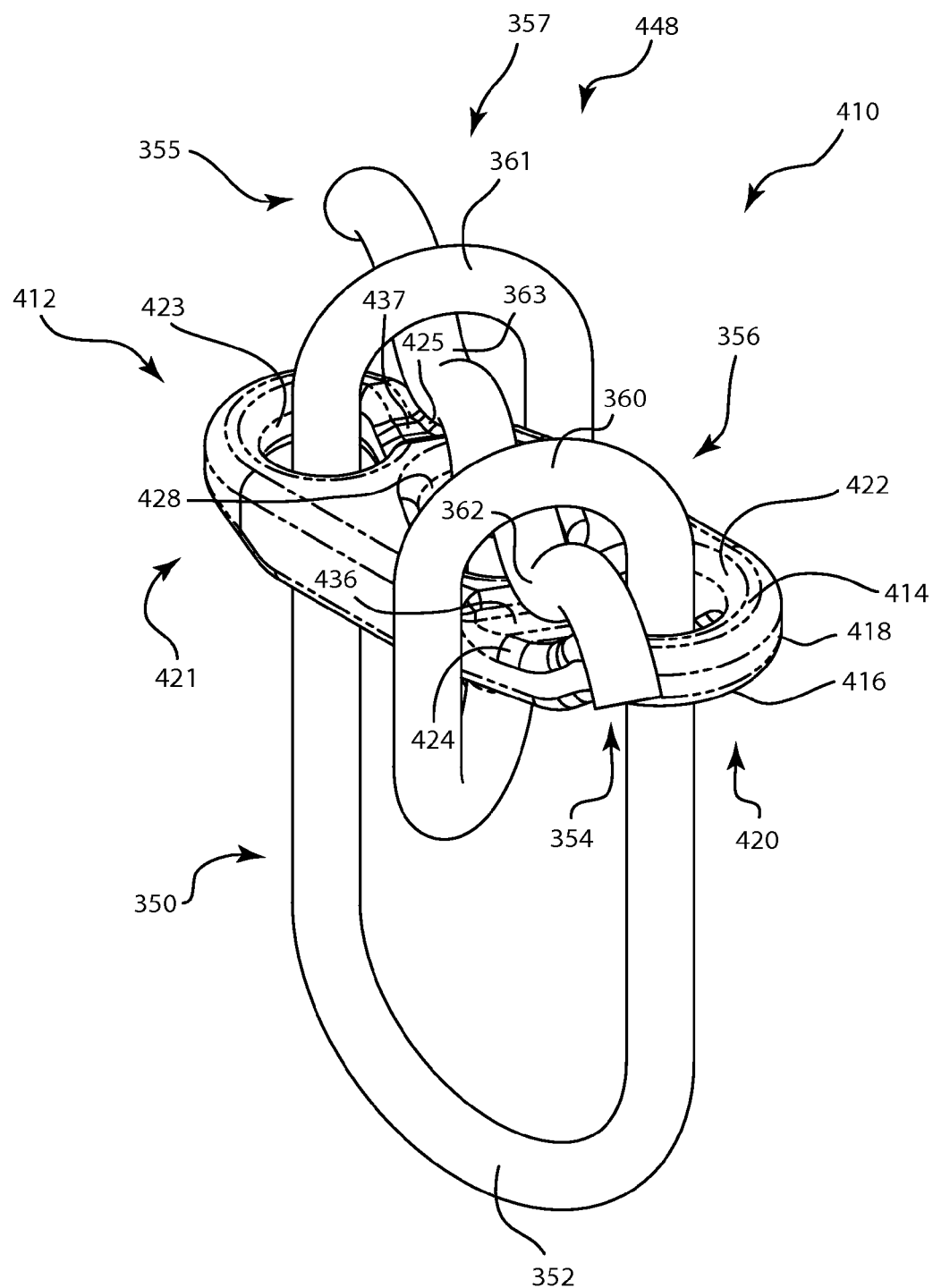
FIG. 23 is a perspective view of the line lock of FIG. 22, with a suture passing loosely through the passageways of the line lock.

Referring to FIG. 23, a perspective view illustrates a system 448 including the line lock 410 of FIG. 22 and a suture 350, like that illustrated in FIGS. 20 and 21. The suture 350 is shown routed relatively loosely through the passageways 422, 423, 424, 425, 428 of the line lock 410.

The suture 350 may be routed through the passageways 422, 423, 424, 425, 428 of the line lock 410 in a manner similar to that of the line lock 310. However, rather than being routed through two different working passageways 328, 329, the locking portions 356, 357 are both routed through the first working passageway 428. From the working passageway 428, the first compressed section 362 of the first working portion 354 extends between the first compression section 360 and the first groove 436, and the second compressed section 363 of the second working portion 355 extends between the second compression section 361 and the second groove 437.

Figure 24:
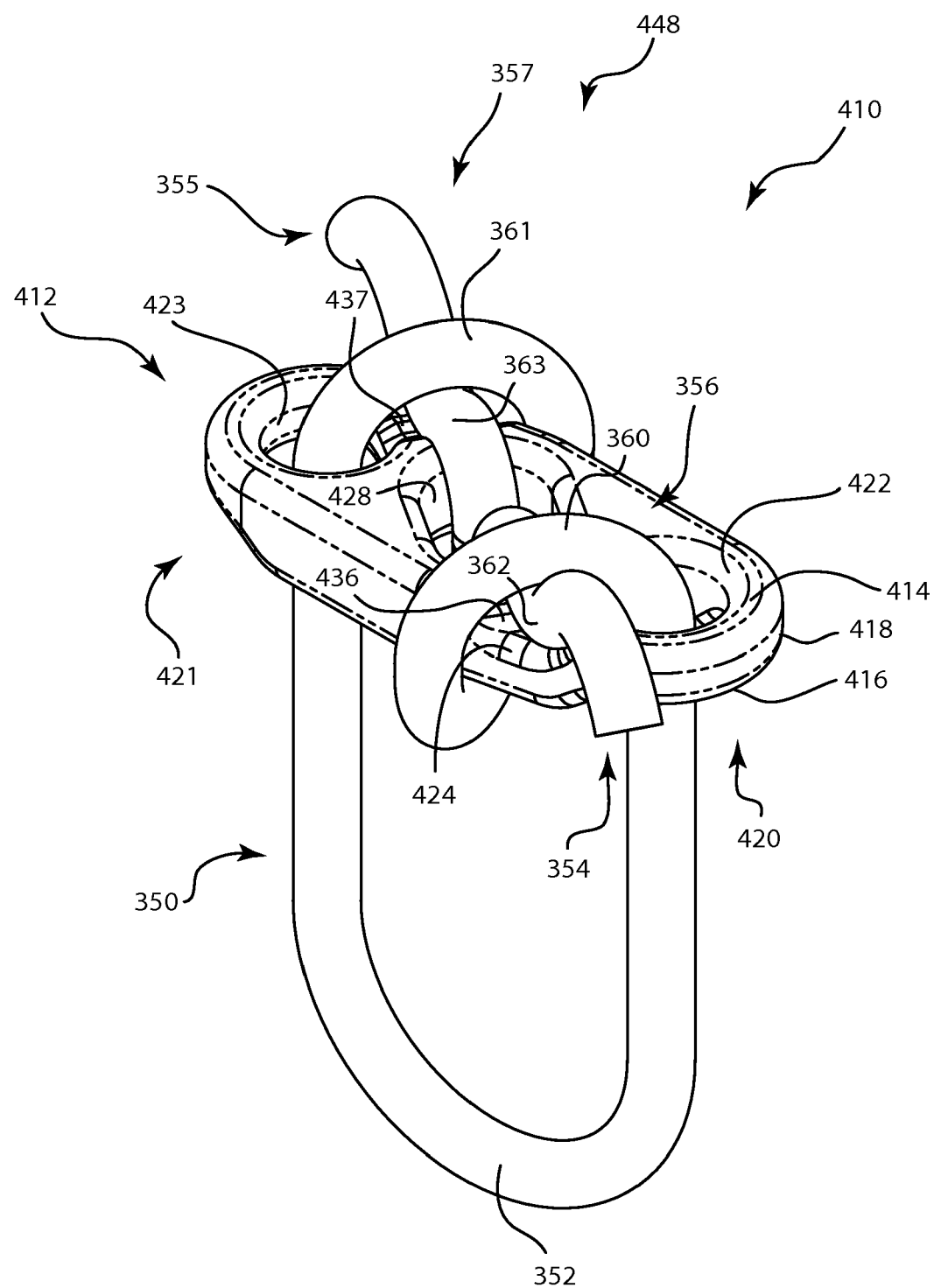
FIG. 24 is a perspective view of the line lock of FIG. 22, with the suture passing tightly through the passageways of the line lock.

Referring to FIG. 24, a perspective view illustrates the system 448 of FIG. 23, with the suture 350 routed relatively tightly through the passageways 422, 423, 424, 425, 428 of the line lock 410. The line lock 410 provides locking in a manner somewhat similar to that of the previous embodiment. More precisely, as the standing portion 352 of the suture 350 is tightened, tension is exerted on the compression sections 360, 361. The compression sections 360, 361 then press the compressed sections 362, 363, respectively, against the top surface 414 to cause the compressed sections 362, 363 to frictionally engage the grooves 436, 437, respectively. As shown, the compression sections 360, 361 may extend generally parallel to the grooves 436, 437 and the compressed sections 362, 363 may extend generally perpendicular to the grooves 436, 437. Accordingly, the working portions 354, 355 form bends where they extend across the grooves 436, 437. The bends enhance locking by adding to the frictional resistance to motion of the working portions 354, 355.

Other aspects of the operation of the line lock 410 are similar to those of the line lock 310 of the previous embodiment. The suture 350 may be inserted into the passageways 422, 423, 424, 425, 428, tightened, and locked within the line lock 410 in any of the ways set forth in connection with the previous embodiment. An insertion tool (not shown) similar to the insertion tool 340 of FIG. 19 may optionally be used to position the line lock 410 and/or move the line lock 410 along the locking portions 356, 357 of the suture 350. Such an insertion tool may have a distal end with an elongated shape that corresponds to that of the body 412 in order to facilitate secure retention of the body 412 against the distal end during the implantation procedure.

As described in connection with the previous embodiment, the working portions 354, 355 may be cut short after the suture 350 has been tightened and locked by the line lock 410. The line lock 410 may also be formed of a variety of bioabsorbable or non-bioabsorbable materials. The text setting forth potential suture threading methods, line lock advancement methods, materials, and the like for the line lock 310 may also apply to the line lock 410 and/or any other embodiment of the invention.

The line lock 410 has the advantage of being relatively compact. The overall dimensions of the body 412 are relatively small, and the volume occupied by the body 412 is also minimal. Accordingly, the line lock 410 may be easily implanted into relatively tight spaces, and if formed of a bioabsorbable material, may be readily absorbed by the body. The linear arrangement of the passageways 422, 423, 428 also keeps the line lock 410 from extending excessively along a direction transverse to that of the pathway followed by the suture 350. In alternative embodiments, only two substantially bounded passageways may be used instead of three. One such embodiment will be shown and described connection with FIGS. 25 through 27.

Figure 25:
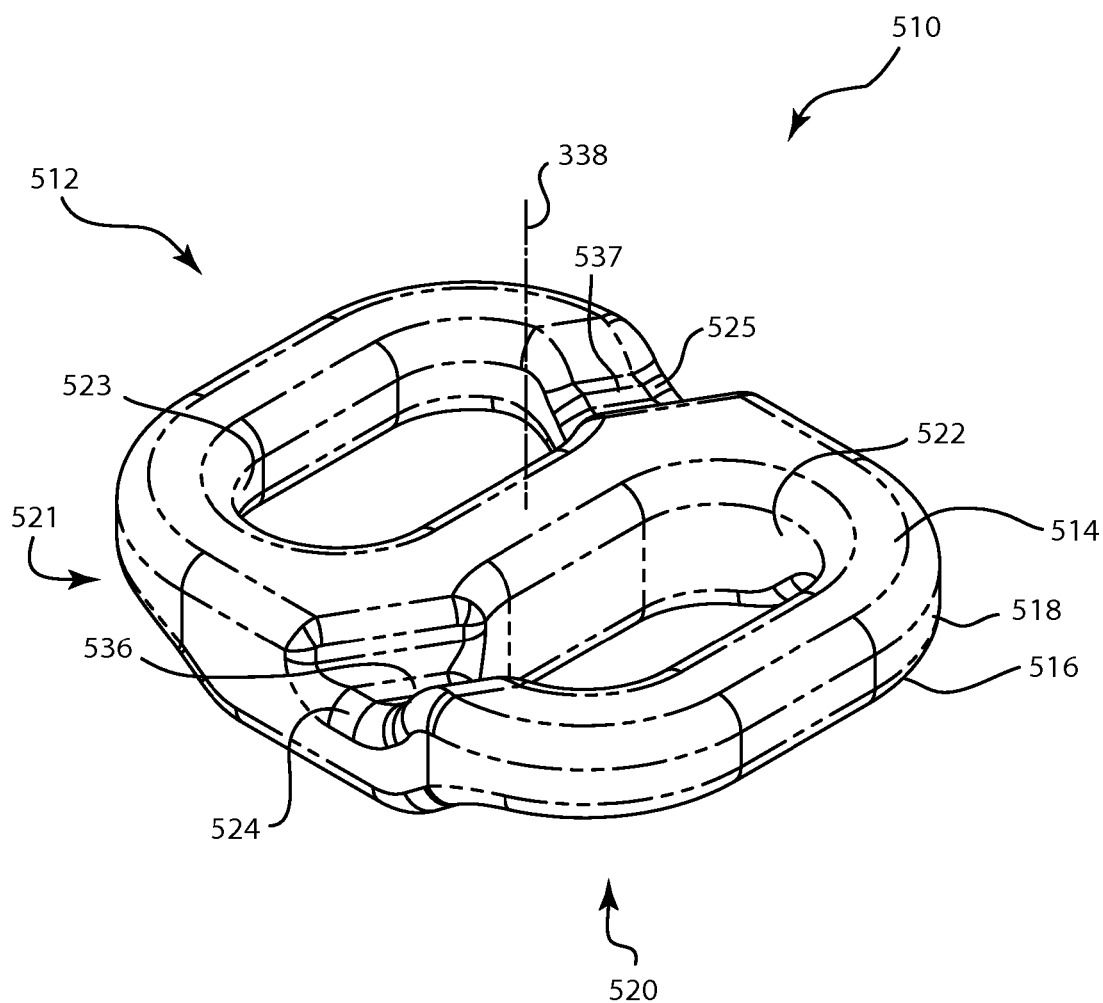
FIG. 25 is a perspective view of a line lock according to yet another alternative embodiment of the invention.

Referring to FIG. 25, a perspective view illustrates a line lock 510 according to another embodiment of the invention. As in the previous embodiment, the line lock 510 has a body 512 with an elongated shape. The body 512 has a top surface 514, a bottom surface 516, and a periphery 518 arranged between the top surface 514 and the bottom surface 516 to define the elongated profile of the body 512. The body 512 bounds a first primary passageway 522, a second primary passageway 523, a first secondary passageway 524, and a second secondary passageway 525. The first and second primary passageways 522, 523 are fully bounded, and the first and second secondary passageways 524, 525 are only partially bounded. No separate working passageway is needed.

The first and second primary passageways 522, 523 are each generally elongated in shape. Accordingly, each of the first and second primary passageways 522, 523 may receive both of the first or second locking portions 356, 357 of the suture 350 (not shown in FIG. 25). This enables the first and second primary passageways 522, 523 to perform the function carried out by the working passageway 428 of the previous embodiment, as will be shown in greater detail in connection with FIGS. 26 and 27.

The body 512 also defines a first groove 536 and a second groove 537, both of which are formed in the top surface 514. The first groove 536 extends along a generally straight path between the first primary and secondary passageways 522, 524. Similarly, the second groove 537 extends along a generally straight path between the second primary and secondary passageways 523, 525. The first and second grooves 536, 537 serve to enhance suture locking by the line lock 510 in a manner similar to the grooves 436, 437 of the previous embodiment.

As shown in FIG. 25, the passageways 522, 523, 524, 525 are symmetrical to each other about a central axis 338 of the body 512. This is because, if rotated 180° about the central axis 338, the first primary and secondary passageways 522, 524 would be superimposed on the second primary and secondary passageways 523, 525.

Figure 26:
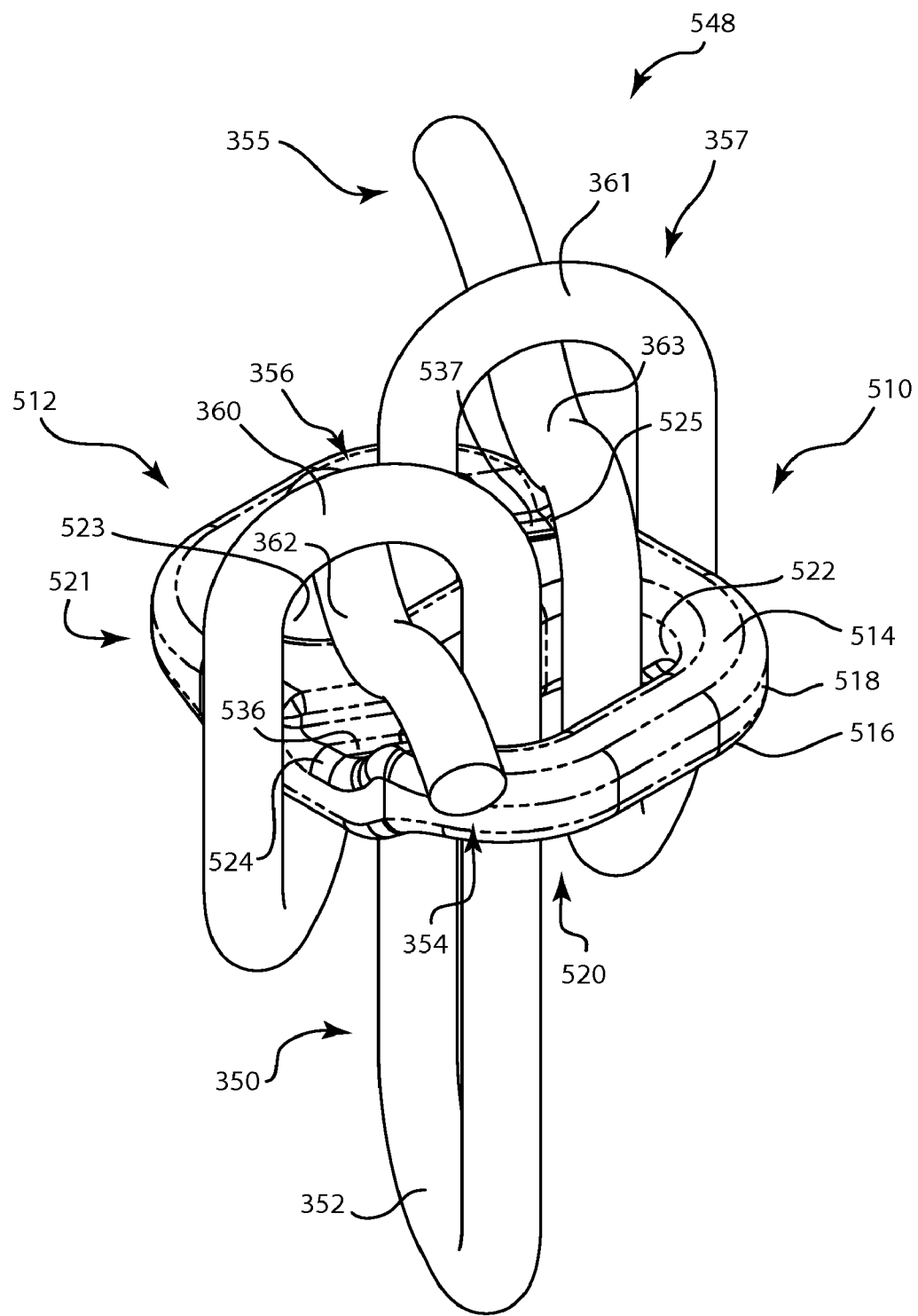
FIG. 26 is a perspective view of the line lock of FIG. 25, with a suture passing loosely through the passageways of the line lock.

Referring to FIG. 26, a perspective view illustrates a system 548 including the line lock 510 of FIG. 25 and a suture 350, like that illustrated in FIGS. 20, 21, 23, and 24. The suture 350 is shown routed relatively loosely through the passageways 522, 523, 524, 525 of the line lock 510.

The suture 350 may be routed through the passageways 522, 523, 524, 525 of the line lock 510 in a manner similar to that of the line lock 410. The first locking portion 356 passes through the first primary passageway 522, then the first secondary passageway 524. The second locking portion 357 passes through the second primary passageway 523, and then the second secondary passageway 525. Then, rather than passing through a working passageway 428, the locking portions 356, 357 are again routed through the first and second primary passageways 522, 523. More precisely, the first locking portion 356 passes through the second primary passageway 523, and the second locking portion 357 passes through the first primary passageway 522. From the second primary passageway 523, the first compressed section 362 of the first working portion 354 extends between the first compression section 360 and the first groove 536, and the second compressed section 363 of the second working portion 355 extends between the second compression section 361 and the second groove 537.

Figure 27:
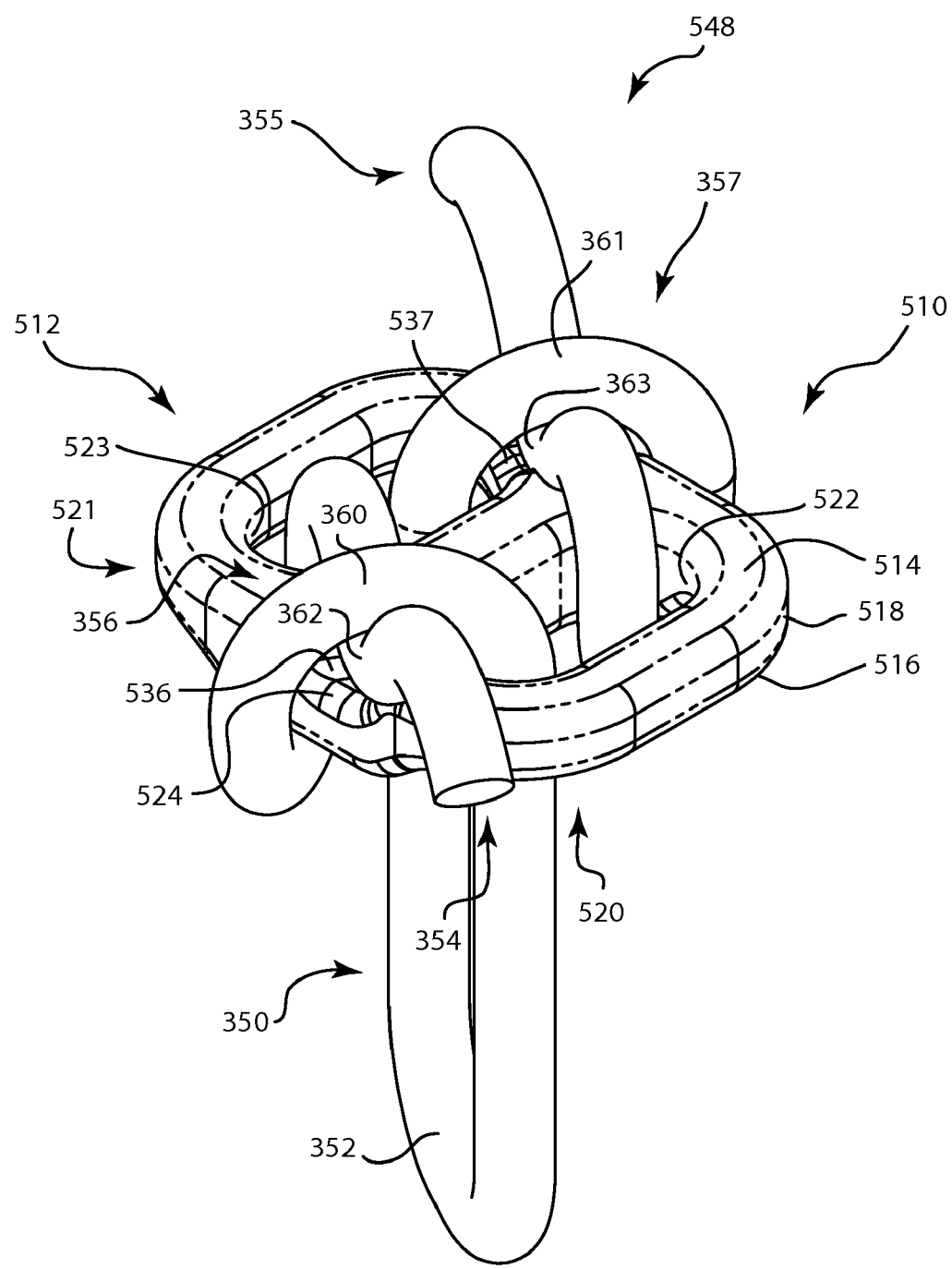
FIG. 27 is a perspective view of the line lock of FIG. 25, with the suture passing tightly through the passageways of the line lock.

Referring to FIG. 27, a perspective view illustrates the system 548 of FIG. 26, with the suture 350 routed relatively tightly through the passageways 522, 523, 524, and 525 of the line lock 510. The line lock 510 provides locking in a manner somewhat similar to that of the previous embodiment. More precisely, as the standing portion 352 of the suture 350 is tightened, tension is exerted on the compression sections 360, 361. The compression sections 360, 361 then press the compressed sections 362, 363, respectively, against the top surface 514 to cause the compressed sections 362, 363 to frictionally engage the grooves 536, 537, respectively. As shown, the compression sections 360, 361 may extend generally parallel to the grooves 536, 537 and the compressed sections 362, 363 may extend generally perpendicular to the grooves 536, 537. Accordingly, the working portions 354, 355 form bends where they extend across the grooves 536, 537. The bends enhance locking by adding to the frictional resistance to motion of the working portions 354, 355.

Other aspects of the operation of the line lock 510 are similar to those of the line locks 310, 410 of the previous two embodiments. The suture 350 may be inserted into the passageways 522, 523, 524, 525, tightened, and locked within the line lock 510 in any of the ways set forth in connection with the previous embodiment. An insertion tool (not shown) similar to the insertion tool 340 of FIG. 19 may optionally be used to position the line lock 510 and/or move the line lock 510 along the locking portions 356, 357 of the suture 350. Such an insertion tool may have a distal end with an elongated shape that corresponds to that of the body 512 in order to facilitate secure retention of the body 512 against the distal end during the implantation procedure.

As described in connection with the embodiment of FIGS. 19 through 21, the working portions 354, 355 may be cut short after the suture 350 has been tightened and locked by the line lock 510. The line lock 510 may also be formed of a variety of bioabsorbable or non-bioabsorbable materials. The text setting forth potential suture threading methods, line lock advancement methods, materials, and the like for the line lock 310 may also apply to the line lock 510 and/or any other embodiment of the invention.

According to one alternative embodiment of the invention, one end of a suture may be removably or permanently secured to a line lock, and the other end may be received by a plurality of passageways in such a manner that the second end is only able to move through the passageways along one direction. The first end may be secured to the line lock via insert molding, knotting, ultrasonic welding, adhesive bonding, or the like. The passageways that receive the second end may be arranged in a manner similar to any of those described in the embodiments set forth above, or equivalents thereof.

The present invention has particular relevance to surgery, and more particularly to tissue retention through the use of sutures. However, the principles, structures, and methods of the present invention may also be extended to other fields, including the use of larger line locks for locking ropes or cables in a wide variety of applications.

While the present invention has application to any need for securing a line, it is particularly advantages to surgical suture applications as a way to conveniently and reliable replace the need to tie suture knots. The advantage is even greater in arthroscopic and endoscopic applications, where sophisticated sliding knots followed by "back-up" knots must be tied outside of a cannula and slid into final position at an internal body site. The sophisticated sliding knots are difficult to tie, time consuming, and bulky. The present invention provides an easy to apply, quick to deliver, and low profile solution that will reliably maintain the desired suture tension.

The present invention may be embodied in other specific forms without departing from its spirit or essential characteristics. For example, above are described various alternative examples of different adjustable line locks. It is appreciated that various features of the line locks can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of retaining a first tissue through the use of a line comprising a first locking portion and an end portion, and a line lock comprising a body that at least partially bounds a plurality of passageways, the method comprising:
    encircling the first tissue with a standing portion of the line, wherein the standing portion is positioned between the first locking portion and the end portion;
    coupling the end portion to the body;
    moving the first locking portion along a first pathway through at least two of the passageways;
    drawing the first locking portion along the first pathway along a first direction; and
    pressing a compressed section of the line against the body with a compression section of the first locking portion in response to tension tending to draw the first locking portion against the first direction, wherein coupling the end portion to the body comprises moving the end portion along a second pathway through at least two of the passageways and drawing the end portion along the second pathway along a second direction.

2. The method of claim 1, wherein drawing the first locking portion along the first pathway along the first direction removes slack from the standing portion.

3. The method of claim 1, wherein drawing the first locking portion along the first pathway along the first direction pushes the compression section away from the compressed section.

4. The method of claim 1, wherein pressing the compressed section of the line against the body prevents lengthening of the standing portion.

5. The method of claim 1, wherein the plurality of passageways comprises a first passageway, a second passageway, and a third passageway, wherein the second passageway is between the first and third passageways, wherein moving the end portion along the second pathway comprises moving the end portion through the second and third passageways.

6. The method of claim 5, wherein at least one of the first and third passageways comprises a slot.

7. The method of claim 6, comprising pressing the compressed section of the line at least partially within the slot with the compression section of the first locking portion.

8. The method of claim 6, wherein the diameter of the slot is no greater than the diameter of the line.

9. The method of claim 6, wherein the slot comprises a first corner, the method comprising biasing the line against the first corner to frictionally lock the line to the line lock.

10. The method of claim 6, wherein the passageway comprising the slot also comprises an enlarged access region which communicates with the slot, the method comprising passing the line through the enlarged access region.

11. The method of claim 10, wherein the enlarged access region comprises a first diameter and the slot comprises a second diameter, wherein the first diameter is larger than the second diameter.

12. The method of claim 11, wherein the first diameter is no less than the diameter of the line.

13. The method of claim 6, wherein each of the first and third passageways comprises a slot.

14. The method of claim 1, wherein each of the passageways is a substantially bounded passageway.

15. The method of claim 1, wherein the second pathway is spaced apart from the first pathway.

16. The method of claim 1, wherein the body comprises a groove, the method comprising pressing the compressed section into the groove.

17. The method of claim 1, wherein the standing portion of the line comprises an adjustable loop, the method comprising encircling the first tissue with the adjustable loop.

18. The method of claim 1, comprising applying further force to the line so as to tension the first locking portion on the line lock.

\* \* \* \* \*